(12) United States Patent
De Clerck

(10) Patent No.: US 11,691,023 B2
(45) Date of Patent: Jul. 4, 2023

(54) HEATABLE IMPLANT DEVICE FOR TUMOR TREATMENT

(71) Applicant: MEDICAL DEVELOPMENT TECHNOLOGIES S.A., Fentange (LU)

(72) Inventor: Luc De Clerck, Fentange (LU)

(73) Assignee: MEDICAL DEVELOPMENT TECHNOLOGIES S.A., Fentange (LU)

( * ) Notice: Subject to any disclaimer, the term of this patent is extended or adjusted under 35 U.S.C. 154(b) by 436 days.

(21) Appl. No.: 16/956,288

(22) PCT Filed: Dec. 19, 2017

(86) PCT No.: PCT/EP2017/083611
§ 371 (c)(1),
(2) Date: Jun. 19, 2020

(87) PCT Pub. No.: WO2019/120489
PCT Pub. Date: Jun. 27, 2019

(65) Prior Publication Data
US 2021/0077821 A1    Mar. 18, 2021

(51) Int. Cl.
*A61N 1/40*      (2006.01)
*A61N 2/00*      (2006.01)
(Continued)

(52) U.S. Cl.
CPC .............. *A61N 1/406* (2013.01); *A61N 2/004* (2013.01); *A61N 2/02* (2013.01); *A61N 1/36002* (2017.08)

(58) Field of Classification Search
CPC .......... A61N 1/406; A61N 2/004; A61N 2/02; A61N 1/36002; A61N 2/002
(Continued)

(56) References Cited

U.S. PATENT DOCUMENTS

| 9,138,293 B1 * | 9/2015 | Weisman ............... A61M 37/00 |
| 2004/0156852 A1 * | 8/2004 | Daum ...................... A61P 9/00 604/20 |

(Continued)

FOREIGN PATENT DOCUMENTS

| WO | WO-03030722 A2 * | 4/2003 | ............. A61N 1/406 |
| WO | WO-03/037202 A1 | 5/2003 | |

(Continued)

OTHER PUBLICATIONS

Enhanced NIR Radiation-Triggered Hyperthermia by Mitochondrial Targeting. Hyo Sung Jung et al. Journal of the American Chemical Society 2015 137 (8), 3017-3023. DOI: 10.1021/ja5122809 (see attached) (Year: 2015).*

(Continued)

*Primary Examiner* — Sunita Reddy
(74) *Attorney, Agent, or Firm* — Clark & Elbing LLP; Susan M. Michaud

(57) ABSTRACT

The present invention concerns a system for treating cancer or tumors by thermotherapy, comprising an expandable implant device, an excitation catheter and an electric power source, wherein the implant device configured for circumferentially subtending a vessel upon expansion of the implant device in said vessel, the implant device comprising a set of cross-connected conductors forming a circumferential structure with openings in between the conductors, said openings having a minimal opening distance when the implant device is expanded of at least 2 mm, wherein the excitation catheter comprises a longitudinal shaft with a distal end, a proximal end, and a longitudinal body in between, whereby the catheter comprises a longitudinal axis along the longitudinal shaft, and whereby the catheter further comprises an emitter coil at or near the distal end, and whereby the longitudinal body of the catheter further comprises a wiring lumen comprising electrical wiring extending (Continued)

from the distal end to the proximal end, and whereby the electrical wiring is connected at or near the distal end with the emitter coil, and wherein the electric power source is connectable, and preferably connected, to the wiring via the proximal end of the catheter shaft for the generation of a time-varying magnetic field with the emitter coil.

12 Claims, 10 Drawing Sheets

(51) Int. Cl.
*A61N 2/02* (2006.01)
*A61N 1/36* (2006.01)

(58) Field of Classification Search
USPC .................................................. 600/1–14
See application file for complete search history.

(56) References Cited

U.S. PATENT DOCUMENTS

| | | |
|---|---|---|
| 2005/0021088 A1 | 1/2005 | Schuler et al. |
| 2005/0090732 A1 | 4/2005 | Ivkov et al. |
| 2006/0041182 A1* | 2/2006 | Forbes ................ A61M 37/00 600/12 |
| 2006/0142748 A1* | 6/2006 | Foreman ................ A61N 2/02 606/27 |
| 2006/0142749 A1* | 6/2006 | Ivkov ................ A61K 49/1818 600/1 |
| 2011/0105825 A1* | 5/2011 | Nayfach-Battilana ....................... A61K 47/6835 600/12 |
| 2013/0053619 A1 | 2/2013 | McKenna et al. |
| 2013/0053620 A1* | 2/2013 | Susedik ................ A61M 37/00 600/10 |
| 2013/0060185 A1* | 3/2013 | Lee ..................... A61M 1/3693 607/103 |
| 2013/0245621 A1 | 9/2013 | Persson et al. |
| 2015/0297281 A1 | 10/2015 | Sutermeister et al. |

FOREIGN PATENT DOCUMENTS

| | | |
|---|---|---|
| WO | WO-2012/130337 A1 | 10/2012 |
| WO | WO-2013/090848 A1 | 6/2013 |
| WO | WO-2018/028804 A1 | 2/2018 |

OTHER PUBLICATIONS

International Search Report and Written Opinion dated Jul. 5, 2018 for PC bnT International Application No. PCT/EP2017/083611, De Clerck, "Heatable Implant Device for Tumor Treatment," filed Dec. 19, 2017 (15 pages).

\* cited by examiner

HEATABLE IMPLANT DEVICE FOR TUMOR TREATMENT

FIELD OF THE INVENTION

The present invention relates to a device, a system and a method for treating cancer and tumors by thermal treatment. Hereby, one or more implant devices are inserted into the body where they can come into contact with or be positioned close to the tumor or cancerous cells, after which the implant devices are heated.

BACKGROUND

Cancer is one of the most leading causes of death in Europe. Statistics from the World Health Organization show that with more than 3.7 million new cases and 1.9 million deaths each year, cancer represents the second most important cause of death and morbidity in Europe. On a global scale, cancer accounted for 8.2 million deaths (around 13% of the total) in 2012. Although more than 40% of cancer deaths can be prevented, cancer accounts for 20% of deaths in the European Region.

Cancer can be treated in a multitude of ways. Whereas in the beginning of cancer treatments, a general approach was applied, whereby cancer was treated on the basis of general rules, in the last decades a patient-specific approach to cancer treatment is being propagated, wherein the selected treatment is prescribed while taking into account patient specifics. In this respect, a cancer patient may be treated using a combination of different treatment options. Hence, there exists an ongoing effort to provide the oncologist or other medical practitioner with additional options for treatment. The present document focuses on such an additional option.

Document US 2005/0021088 A1 discloses systems for the application of heat to an area of the body of a mammal, a system including a device fabricated from or coated with a material comprising of a non-metal matrix and susceptor particles, a non-invasive inductor and magnetic circuit for heating the particles by transmitting an alternating magnetic field (AMF), and an alternating current generator that provides an alternating current to the inductor.

Document WO 2012/130337 A1 discloses systems, devices and methods for the ablation of a vessel's wall from the inside, more specifically to implant devices and to the ablation of the wall of one or more pulmonary veins (PV) from the inside, preferably transmural ablation and preferably at the level of the antrum. Hereby, one or more implant devices can be implanted in the vessels and can subsequently be heated by external energy-providing means. This document is related particularly to the treatment of atrial fibrillation by pulmonary vein isolation. Hereby, a transmural circumferential lesion in a large vessel is intended. The system of WO 2012/130337 is designed for treating atrial fibrillation by pulmonary vein isolation, but is not specifically designed for treating tumors or cancers.

Document US 2005/0090732 A1 discloses compositions, systems and methods for treating a subject's body, body part, tissue, body fluid cells, pathogens, or other undesirable matter involving the administration of a targeted thermotherapy that comprises a bioprobe (energy susceptive materials that are attached to a target-specific ligand). One important problem is that these bioprobes may be present throughout the body and that it is not always easy to heat the bioprobes efficiently.

The present invention aims to resolve at least some of the problems and disadvantages mentioned above. The aim of the invention is to provide a method and system which allow efficient heating of implants at specific locations in the human or animal body in the treatment of cancer or tumors.

SUMMARY OF THE INVENTION

The present invention and embodiments thereof serve to provide a solution to one or more of above-mentioned disadvantages. To this end, the present invention relates to a system according to claim 1 and a method according to claim . . . . Further embodiments are disclosed in the other claims and further in the present document.

The system for treating cancer or tumors by thermotherapy of the present invention, comprises an expandable implant device, an excitation catheter and an electric power source. Herein, the implant device is configured for circumferentially subtending a vessel upon expansion of the implant device in said vessel, the implant device comprising a set of cross-connected conductors forming a circumferential structure with openings in between the conductors, said openings having a minimal opening distance when the implant device is expanded of at least 2 mm, the excitation catheter comprises a longitudinal shaft with a distal end, a proximal end, and a longitudinal body in between, whereby the catheter comprises a longitudinal axis along the longitudinal shaft, and whereby the catheter further comprises an emitter coil at or near the distal end, and whereby the longitudinal body of the catheter further comprises a wiring lumen comprising electrical wiring extending from the distal end to the proximal end, and whereby the electrical wiring is connected at or near the distal end with the emitter coil, and the electric power source is connectable, and preferably connected, to the wiring via the proximal end of the catheter shaft for the generation of a time-varying magnetic field with the emitter coil.

In a preferred embodiment, the system comprises a set of bioprobes, each bioprobe comprising a magnetic susceptor and at least one ligand.

The present invention also concerns a method for treating a tumor or cancerous cells in a patient by thermotherapy, comprising the steps of:

implanting an expandable implant device in a vessel such that the implant device circumferentially subtends the vessel upon expansion of the implant device in said vessel, the implant device comprising a set of cross-connected conductors forming a circumferential structure with openings in between the conductors, said openings having a minimal opening distance when the implant device is expanded of at least 2 mm, whereby the vessel and the implant position of the implant device in the vessel is pre-selected on the basis of distance to the tumor or cancerous cells and/or on the basis of nutrient supply flow to the tumor or cancerous cells;

inserting an excitation catheter in the patient, wherein the excitation catheter comprises a longitudinal shaft with a distal end, a proximal end, and a longitudinal body in between, whereby the catheter comprises a longitudinal axis along the longitudinal shaft, and whereby the catheter further comprises an emitter coil at or near the distal end, and whereby the longitudinal body of the catheter further comprises a wiring lumen comprising electrical wiring extending from the distal end to the proximal end, and whereby the electrical wiring is connected at or near the distal end with the emitter coil, positioning the emitter coil of the catheter nearby and preferably within the expanded implant device, and energizing the emitter coil to emit an alternating magnetic field in response to which a current flows in the conductors of the implant device, thereby heating the implant device and re-radiating an alternating magnetic field to surrounding tissue.

In a preferred embodiment, the method comprising the steps of inserting a set of bioprobes into the patient, whereby each bioprobe comprises a magnetic susceptor and at least one ligand, allowing said bioprobes to attach to a target and energizing the emitter coil, thereby heating bioprobes in the vicinity of the emitter coil and of the expandable implant device.

The present invention allows cancer or tumor treatment by thermotherapy in two or more ways. Firstly, the implant device itself is heated during energizing of the emitter coil. This can be achieved by inductive heating, whereby the AMF generated by the emitter coil induces a, preferably circumferential, current in the conductors of the implant device which heats up due to e.g. Joule heating. Note that in a preferred embodiment, the implant device comprises magnetic material such as ferromagnetic, antiferromagnetic and/or ferromagnetic material, which may be heated due to hysteresis effects. Due to the direct and intimate contact of the implant device with the vessel inner wall, heat is transferred from the implant device to the surrounding tissue. It has been observed that cancerous cells respond worse to heat than healthy cells. Furthermore, by implanting the implant device at a position near the tumor or cancer cells, thereby inducing cell death upon heating of the implant due to necrosis by thermo-ablation and/or a heat-shock response. Alternatively, if the implant is positioned in e.g. a blood vessel upstream the tumor, the provision of nutrients to the tumor can be seriously affected by the increased temperature. Secondly, the implant device acts as an electromagnetic wave diffuser due to its cross-connected conductors and openings therebetween. Hereby, the implant device acts as antenna for re-radiating the AMF generated by the emitter coil, thereby effectively diffusing the original AMF. As a result, the AMF is distributed more evenly over the surrounding tissue, thereby reducing the appearance of hotspots in the surrounding tissue.

In a preferred embodiment, the set of bioprobes bind to target sites and heat up if exposed to an AMF, thereby clearly providing an additional advantage. These bioprobes comprise a magnetic susceptor, making the bioprobe heat up due to hysteresis, which is much more efficient than inductive heating via the Joule effect. Hence, the presence of bioprobes at the target zones, render these target zone into effective hotspots.

Preferred embodiments of the system and method are discussed in any of the dependent claims and further below.

DESCRIPTION OF FIGURES

The following description of the figures of specific embodiments of the invention is merely exemplary in nature and is not intended to limit the present teachings, their application or uses. Throughout the drawings, corresponding reference numerals indicate like or corresponding parts and features.

DETAILED DESCRIPTION OF THE INVENTION

Figure 1:
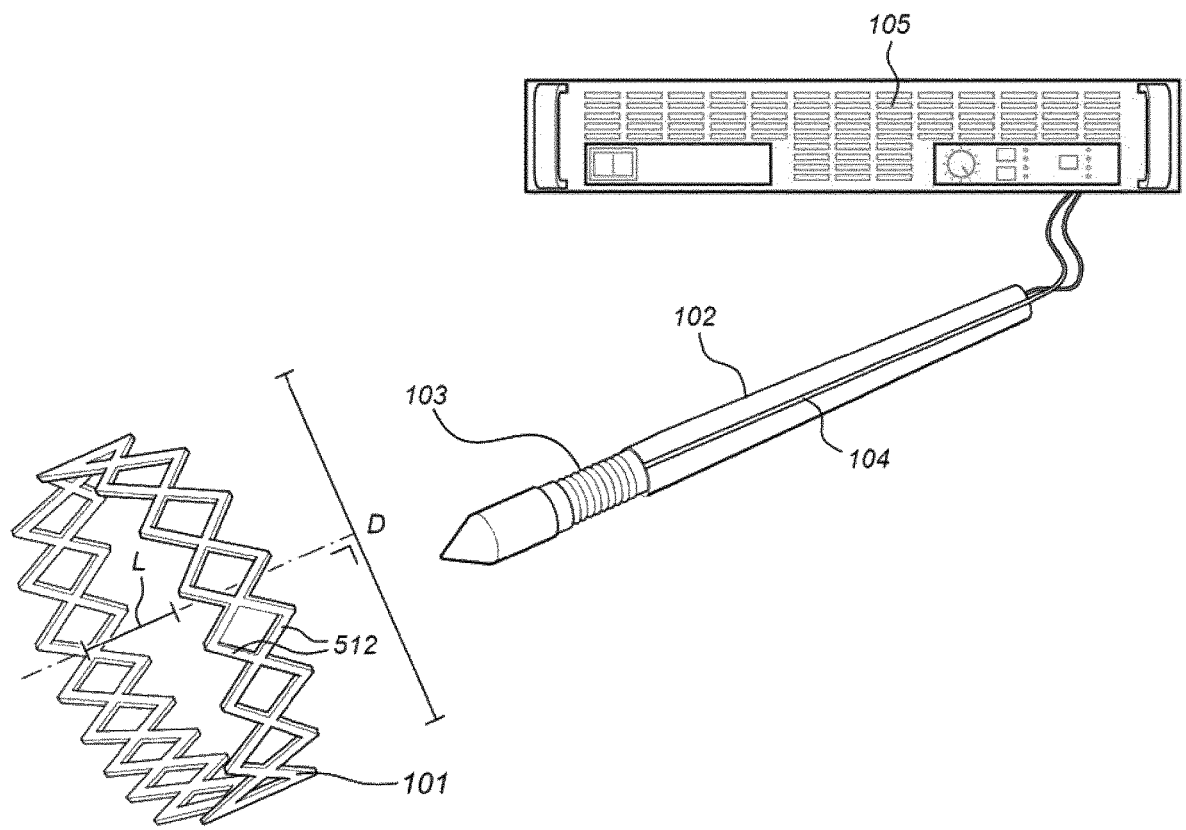
FIG. 1 shows a schematic representation of an embodiment of the system of the present invention.

The present invention concerns a system and method for treating a tumor or cancerous cells in a patient by thermotherapy.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise", "comprising", and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

Furthermore, the terms first, second, third and the like in the description and in the claims, are used for distinguishing between similar elements and not necessarily for describing a sequential or chronological order, unless specified. It is to be understood that the terms so used are interchangeable under appropriate circumstances and that the embodiments of the invention described herein are capable of operation in other sequences than described or illustrated herein.

The recitation of numerical ranges by endpoints includes all numbers and fractions subsumed within that range, as well as the recited endpoints.

The expression "% by weight", "weight percent", "% wt" or "wt %", here and throughout the description unless otherwise defined, refers to the relative weight of the respective component based on the overall weight of the formulation.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any 3, 4, 5, 6 or etc. of said members, and up to all said members.

The term "bioprobe", as used herein, refers to a composition comprising a susceptor and at least one ligand. The ligand acts to guide the bioprobe to a target.

The term "susceptor", as used herein, refers to a particle (optionally comprising a coating) of a material that, when exposed to an energy source, either heats or physically moves. Similarly, the term "magnetic susceptor" refers to such particles wherein the energy source to which the particles respond is an alternating magnetic field (AMF).

The term "ligand", as used herein, refers to a molecule or compound that attaches to a susceptor (or a coating on the susceptor) and targets and attaches to a biological marker. A monoclonal antibody specific for Her-2 (an epidermal growth factor receptor protein) is an exemplary ligand.

The term "target", as used herein, refers to the matter for which deactivation, rupture, disruption or destruction is desired, such as a diseased cell, a pathogen, or other undesirable matter. A marker may be attached to the target. Breast cancer cells are exemplary targets.

The term "marker", as used herein, refers to an antigen or other substance to which the bioprobe ligand is specific. Her-2 protein is an exemplary marker.

The term "bioprobe system", as used herein, refers to a bioprobe specific to a target that is optionally identified via a marker.

The term "indication", as used herein, refers to a medical condition, such as a disease. Breast cancer is an exemplary indication.

The term "AMF" (an abbreviation for alternating magnetic field), as used herein, refers to a magnetic field that changes the direction of its field vector periodically, for example in a manner that is sinusoidal, triangular, or rectangular. The AMF may also be added to a static magnetic field, such that only the AMF component of the resulting magnetic field vector changes direction. It will be appreciated that an alternating magnetic field is accompanied by an alternating electric field and is electromagnetic in nature.

The term "RF" (an abbreviation for radio frequency), as used herein, refers to a radio frequency in the range from about 0.1 Hz to about 900 MHz.

The term "duty cycle", as used herein, refers to the ratio of the time that the energy source is on to the total time that the energy source is on and off in one on-off cycle.

The term "hyperthermia", as used herein, refers to heating of tissue to temperatures above 40° C., preferably above 43° C., still more preferably above about 47° C., and preferably limited to below 60° C., more preferably limited to 55° C., still more preferably limited to 51° C.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention. The terms or definitions used herein are provided solely to aid in the understanding of the invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In a first aspect, the invention provides a system for treating a tumor or cancerous cells in a patient by thermotherapy. The system comprises an expandable implant device, an excitation catheter and an electric power source which are interconnectable as discussed further.

FIG. 1 shows a schematic representation of an embodiment of the system of the present invention. The figure shows an expandable implant device (101), a catheter (102) comprising an emitter coil (103) at the distal end, electrical wiring (104) extending from the distal end to the proximal end of the catheter, and connected at the distal end with the emitter coil 103 and at the proximal end with an electric power source 105.

The implant device (101) is radially expandable, such that it can circumferentially subtend a vessel upon expansion of the implant device in said vessel. The radially expandable implant of FIG. 1 comprises a set of cross-connected conductors (512) forming a circumferential structure with openings in between the conductors, said openings having a minimal opening distance when the implant device is expanded of at least 2 mm.

Figure 2:
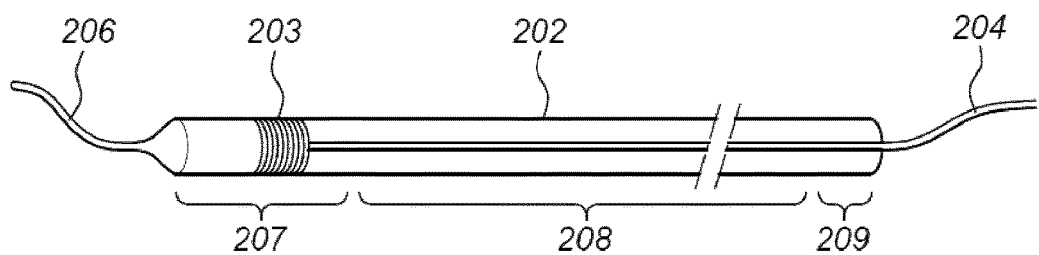
FIG. 2 schematically represents an embodiment of a catheter according to the present invention.

FIG. 2 schematically represents an embodiment of a catheter according to the present invention, comprising a longitudinal shaft 202 with a distal end 207, a proximal end 209, and a longitudinal body 208 in between, the distal end 207 of the catheter shaft comprising an emitter coil 203 and a guiding tip 206. The emitter coil 203 is connected to electrical wiring 204 extending from the distal end to the proximal end.

In an embodiment of the present invention, the catheter shaft has a guiding lumen suitable for sliding the catheter over a guidewire.

Figure 3:
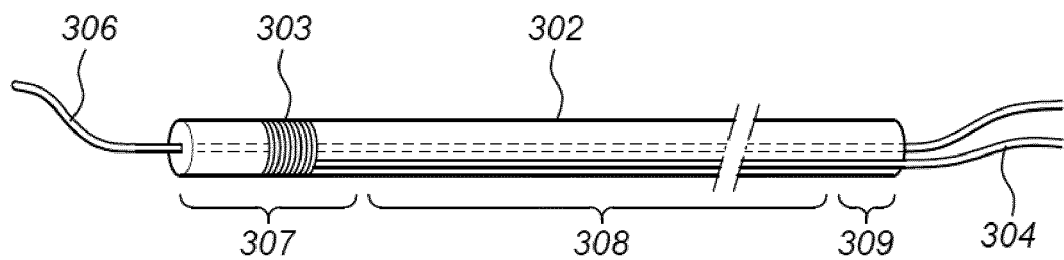
FIG. 3 schematically represents a guidewire 306 and an embodiment of a catheter according to the present invention.

FIG. 3 schematically represents a guidewire 306 and an embodiment of a catheter according to the present invention, comprising a longitudinal shaft 302 with a distal end 307, a proximal end 309, and a longitudinal body 308 in between, the distal end 307 of the catheter shaft comprising an emitter coil 303. The emitter coil 303 is connected to electrical wiring 304 extending from the distal end to the proximal end. The catheter shaft has a guiding lumen suitable for sliding the catheter over the guidewire 306.

Figure 4:
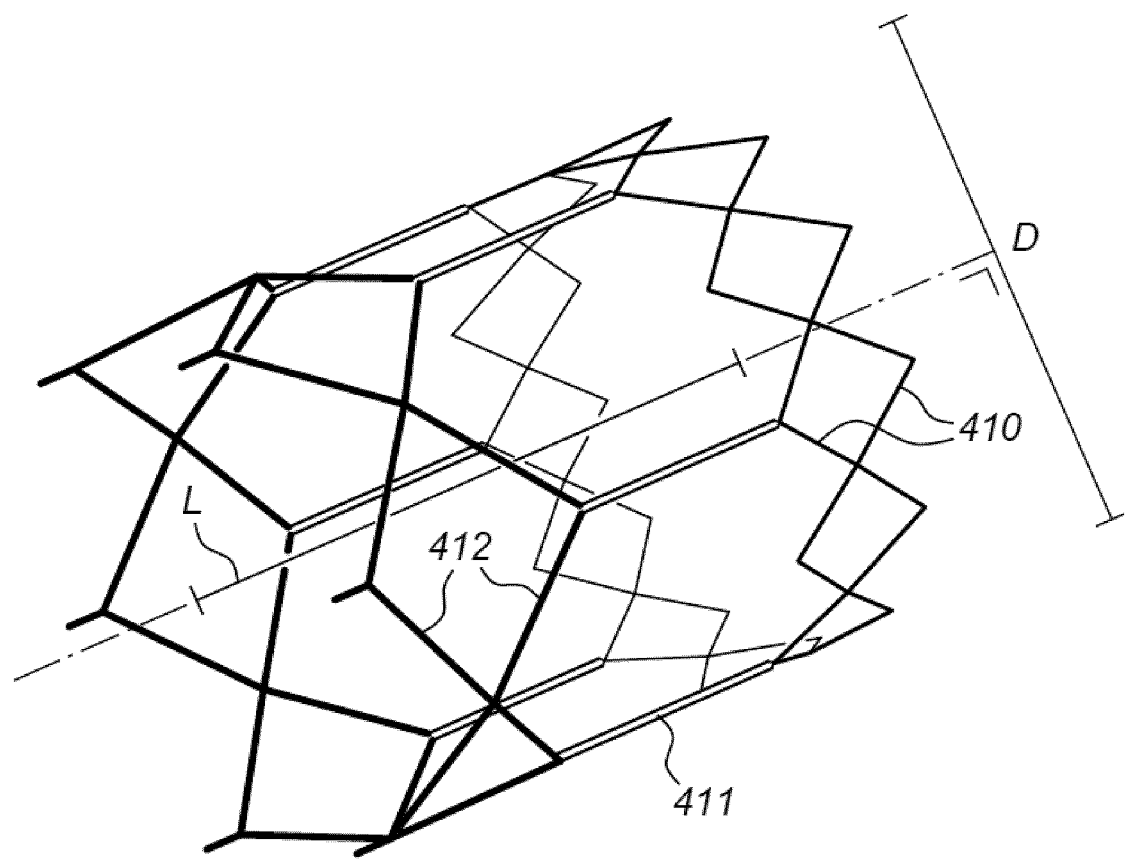
FIG. 4 schematically represents another embodiment of an implant device according to the present invention.

FIG. 4 schematically represents another embodiment of an implant device according to the present invention. This implant device, as well as the implant device depicted in FIG. 1, comprises a central axis L, and is radially expandable in directions perpendicular to the central axis. The implant device in FIG. 4 comprises a radially expandable heating region 412 and a radially expandable ring of open diamond-shaped elements 410 which are connected to the heating region by struts 411. The heating region 412 may comprise a set of wide conductors which can make good thermal contact with surrounding tissue and for which the heat generation due to an induced current and Joule heating, can be optimized. The struts 411 and ring 410 can be made of smaller thicknesses than the conductors of the heating region, thereby reducing the induced current, leading to lesser heating. Nevertheless, the struts and ring act as diffusers of the electromagnetic field generated by the emitter coil of the catheter.

In an embodiment, the implant device comprises, and preferably consists of, bioresorbable material.

In an embodiment of the present invention, the emitter coil comprises a flux-enhancing material.

In a preferred embodiment of the present invention, the emitter coil comprises a central axis substantially parallel to the longitudinal axis of the catheter.

In a preferred embodiment, the system comprises a set of bioprobes. These bioprobes comprise magnetic energy susceptive material, preferably one or more magnetic energy susceptive particles.

In a preferred embodiment, the bioprobes comprise a ligand which targets mitochondria, preferably the ligand binding to peripheral benzodiazepine receptors (PBR) or mitochondrial benzodiazepine receptors (MBR). Exemplary ligands are Ro5-4864, PK11195, PK01195 and PK14105.

In a preferred embodiment, the implant device comprises cavities, preferably at an outer surface of the implant device, said cavities provided with one or more bioprobes, and said cavities closed off with a thermodegradable cover, e.g. a thermoactive coating, whereby the bioprobes can be released from the cavities upon heating of the implant device, preferably after the implant device has been well positioned in the vessel and more preferably after the implant has grown into the surrounding tissue. The release of the bioprobes can hereby occur gradually, depending upon duration of the energizing and the obtained temperature of the implant device. This can be enabled by providing cavities of different depths and/or by covering cavities with different thicknesses of the thermodegradable cover.

Figure 5A:
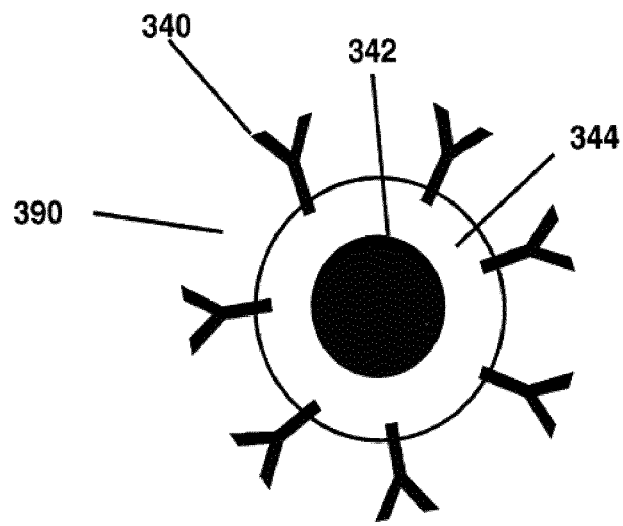
FIG. 5A discloses a bioprobe configuration according to an embodiment of the present invention.

FIG. 5A discloses a bioprobe configuration according to an embodiment of the present invention. A bioprobe 390 comprises a magnetic energy susceptive particle 342. The magnetic particle 342, also referred to as a susceptor, may include a coating 344. Coating 344 may fully or partially coat susceptor 342. At least one targeting ligand 340, such as, but not limited to, an antibody, may be located on an exterior portion of bioprobe 390. The targeting ligand 340 may be selected to seek out and attach to a target, such as a particular type of cell or disease matter. Heat is generated in the susceptor 342 when susceptor 342 is exposed to an energy source, such as AMF. Coating 344 may enhance the heating properties of bioprobe 390, particularly if coating 344 has a high viscosity, for example, is a polymeric material.

In a general sense, this heat represents an energy loss as the magnetic properties of the material are forced to oscillate in response to the applied alternating magnetic field. The amount of heat generated per cycle of magnetic field and the mechanism responsible for the energy loss depend on the specific characteristics of both the susceptor 342 and the magnetic field. Susceptor 342 heats to a unique temperature, known as the Curie temperature, when subjected to an AMF. The Curie temperature is the temperature of the reversible ferromagnetic to paramagnetic transition of the magnetic material. Below this temperature, the magnetic material heats in an applied AMF. However, above the Curie temperature, the magnetic material becomes paramagnetic and its magnetic domains become relatively unresponsive to the AMF. Thus, the material does not generate heat when exposed to the AMF above the Curie temperature. As the material cools to a temperature below the Curie temperature, it recovers its magnetic properties and resumes heating, as long as the AMF remains present. This cycle may be repeated continuously during exposure to the AMF. Thus, magnetic materials are able to self-regulate the temperature of heating. The temperature to which susceptor 342 heats is dependent upon, inter alia, the magnetic properties of the material, characteristics of the magnetic field, and the cooling capacity of the target site. Selection of the magnetic material and AMF characteristics may be tailored to optimize treatment efficacy of a particular tissue or target type. In an embodiment of the present invention, the magnetic material may be selected to possess a Curie temperature between about 38° C. and about 60° C.

Many aspects of susceptor 342, such as material composition, size, and shape, directly affect heating properties. Many of these characteristics may be designed simultaneously to tailor the heating properties for a particular set of conditions found within a tissue type. For example, for susceptor 342, the most desirable size range depends upon the particular application and on the material(s) comprising susceptor 342.

The size of susceptor 342 determines the total size of bioprobe 390. Bioprobes 390 that are to be injected may be spherical and may be required to have a long residence time in the bloodstream, i.e., avoid sequestration by the liver and other non-targeted organs. Bioprobe 390 may be successful in avoiding sequestration if its total diameter is less than about 30 nm. If bioprobe 390 contains a magnetite ($Fe_3O_4$) particle 342, then a diameter of susceptor 342 may be between about 8 nm and about 20 nm. In this case, bioprobes 390 may be sufficiently small to evade the liver, and yet the magnetic particle 342 still retains a sufficient magnetic moment for heating in an applied AMF. Magnetite particles larger than about 8 nm generally tend to be ferrimagnetic and thus appropriate for disease treatment. If other elements, such as cobalt, are added to the magnetite, this size range can be smaller. This results directly from the fact that cobalt generally possesses a larger magnetic moment than magnetite, which contributes to the overall magnetic moment of cobalt-containing susceptor 342. In general, the size of bioprobe 390 may be about 0.1 nm to about 250 nm, depending upon the disease indication and bioprobe composition.

Examples of susceptors for use herein include iron oxide particles and $FeCo/SiO_2$ particles. Some susceptors have a specific absorption rate (SAR) of about 310 Watts per gram of particle at 1300 Oerstedt flux-density and 150 kHz frequency, such as series EMG700 and EMG1111 iron oxide particles of about 110 nm diameter available from Ferrotec Corp. (Nashua, N.H.). Other particles have a SAR of about 400 Watts per gram of particle under the same magnetic field conditions, such as the $FeCo/SiO_2$ particles available from Inframat Corp. (Willington, Conn.).

While determining the size of susceptor 342, its material composition may be determined based on the particular target. Because the self-limiting temperature of a magnetic material, or the Curie temperature, is directly related to the material composition, as is the total heat delivered, magnetic particle compositions may be tuned to different tissue or target types. This may be required because each target type, given its composition and location within the body, possesses unique heating and cooling capacities. For example, a tumor located within a region that is poorly supplied by blood and located within a relatively insulating region may require a lower Curie temperature material than a tumor that is located near a major blood vessel. Targets that are in the bloodstream will require different Curie temperature materials as well. Thus, in addition to magnetite, particle compositions may contain elements such as cobalt, iron, rare earth metals, etc.

The presence of coating 344 and the composition of the coating material may form an integral part of the energy loss, and thus the heat produced, by bioprobes 390. In addition, coating 344 may serve additional purposes. The coating 344 does not have to cover the whole bioprobe core 342, but may only partially cover the core 342. Coating 344 may provide a biocompatible layer separating the magnetic material from the immunologic defenses in a patient, thereby controlling the residence time of the particles in the blood or tissue fluids.

This control of residence time allows one to choose targeting ligands 340 that are best suited for a particular tissue type. In addition, coating 344 may serve to protect the patient from potentially toxic elements in susceptor 342. A second function of the coating materials may be the prevention of particle aggregation, as bioprobes 390 may be suspended in a fluid. It may be also be advantageous to coat bioprobe 390 with a biocompatible coating that is biodegradable or resorbable. In such an application, both the coating 344 and the susceptor 342 may be digested and absorbed by the body.

Suitable materials for the coating 344 include synthetic and biological polymers, copolymers and polymer blends, and inorganic materials. Polymer materials may include acrylates, siloxanes, styrenes, acetates, alkylene glycols, alkylenes, alkylene oxides, parylenes, lactic acid, glycolic acid, and combinations thereof. Further suitable coating materials include a hydrogel polymer, a histidine-containing polymer, and a combination of a hydrogel polymer and a histidine-containing polymer.

Coating materials may include biological materials such as polysaccharides, polyaminoacids, proteins, lipids, glycerols, fatty acids, and combinations thereof. Other biological materials for use as a coating material may include heparin, heparin sulfate, chondroitin sulfate, chitin, chitosan, cellulose, dextran, alginate, starch, carbohydrate, and glycosaminoglycan. Proteins may include an extracellular matrix protein, proteoglycan, glycoprotein, albumin, peptide, and gelatin. These materials may also be used in combination with any suitable synthetic polymer material.

Inorganic coating materials may include any combination of a metal, a metal alloy, and a ceramic. Examples of ceramic materials include hydroxyapatite, silicon carbide, carboxylate, sulfonate, phosphate, ferrite, phosphonate, and oxides of Group IV elements of the Periodic Table of Elements. These materials may form a composite coating that also contains biological or synthetic polymers. Where susceptor 342 is formed from a magnetic material that is biocompatible, the surface of the particle itself operates as the biocompatible coating.

The coating 344 material may also serve to facilitate transport of bioprobe 390 into a cell, a process known as transfection. Such coating materials, known as transfection agents, may include vectors, prions, polyaminoacids, cationic liposomes, amphiphiles, non-liposomal lipids, or any combination thereof. A suitable vector may be a plasmid, a virus, a phage, a viron, or a viral coat. The bioprobe coating may be a composite of a combination of transfection agents with organic and inorganic materials, such that the particular combination may be tailored for a particular type of a diseased cell and a specific location within a patient's body.

To ensure that bioprobe 390 selectively attaches to, or otherwise associates with, the target, an appropriate ligand 340 may be combined with bioprobe 390. The association of a ligand or ligands with bioprobes 390 allows for targeting of cancer or disease markers on cells. It also allows for targeting biological matter in the patient. The term ligand relates to compounds which may target molecules including, for example, proteins, peptides, antibodies, antibody fragments, saccharides, carbohydrates, glycans, cytokines, chemokines, nucleotides, lectins, lipids, receptors, steroids, neurotransmitters, Cluster Designation/Differentiation (CD) markers, imprinted polymers, and the like. Examples of protein ligands include cell surface proteins, membrane proteins, proteoglycans, glycoproteins, peptides, and the like. Example nucleotide ligands include complete nucleotides, complimentary nucleotides, and nucleotide fragments. Example lipid ligands include phospholipids, glycolipids, and the like. Ligand 340 may be covalently bonded to or physically interacted with susceptor 342 or coating 344. Ligand 340 may be bound covalently or by physical interaction to an uncoated portion of susceptor 342. Ligand 340 may be bound covalently or by physical interaction directly to an uncoated portion of susceptor 342 and partially covered by coating 344. Ligand 340 may be bound covalently or by physical interaction to a coated portion of bioprobe 390. Ligand 340 may be intercalated to the coated portion of bioprobe 390.

Covalent bonding may be achieved with a linker molecule. The term "linker molecule", as used herein, refers to an agent that targets particular functional groups on ligand 340 and on susceptor 342 or coating 344, and thus forms a covalent link between ligand 340 and susceptor 342 or coating 344. Examples of functional groups used in linking reactions include amines, sulfhydryls, carbohydrates, carboxyls, hydroxyls, and the like.

The linking agent may be a homobifunctional or heterobifunctional crosslinking reagent, for example, carbodiimides, sulfo-NHS esters linkers, and the like. The linking agent may also be an aldehyde crosslinking reagent, such as glutaraldehyde. The linking agent may be chosen to link ligand 340 to susceptor 342 or coating 344 in a preferable orientation, specifically with the active region of the ligand 340 available for targeting. Physical interaction does not require that the linking molecule and ligand 340 be bound directly to susceptor 342 or to coating 344 by non-covalent means such as, for example, absorption, adsorption, or intercalation.

Figure 6:
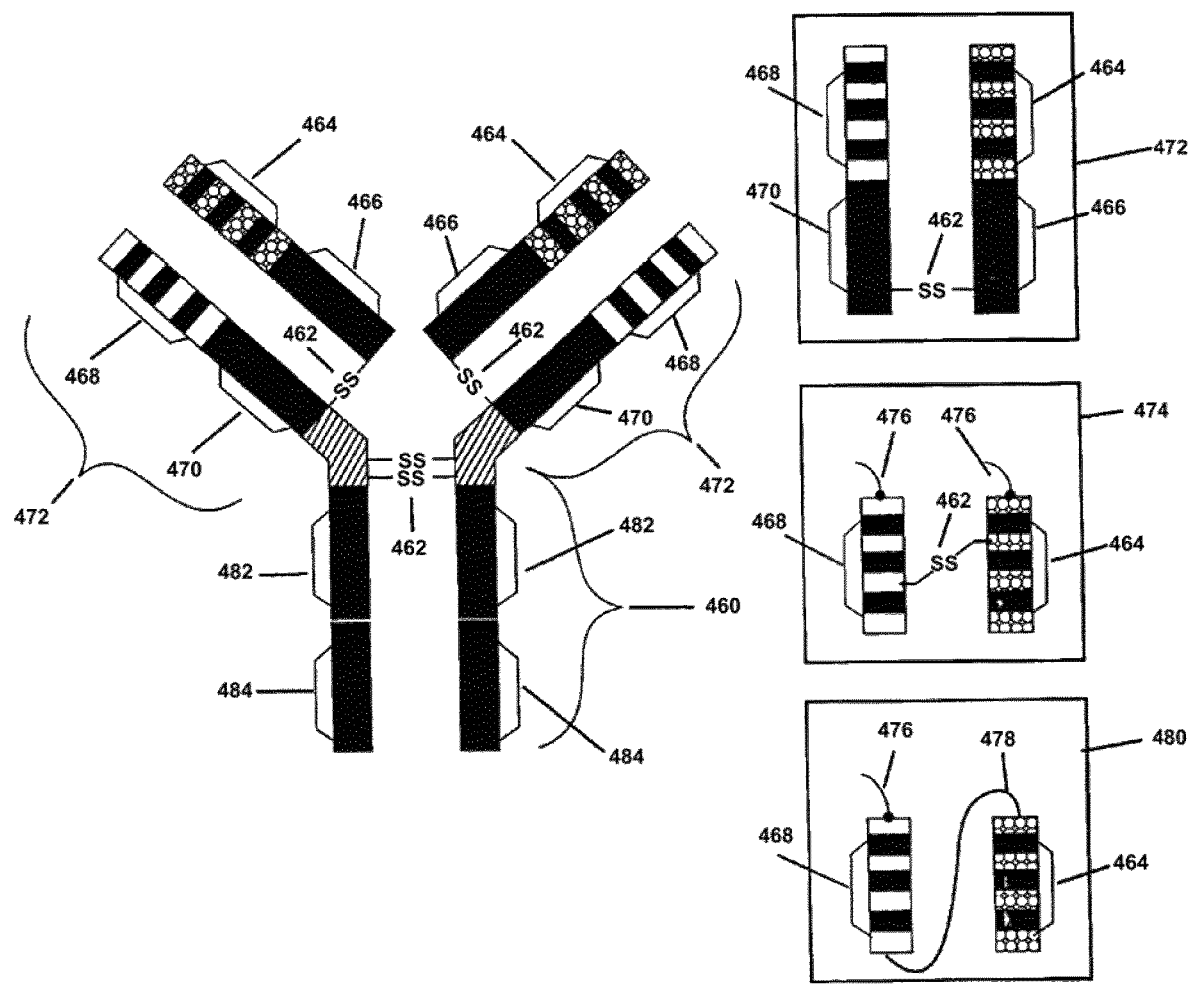
FIG. 6 schematically illustrates an example of a ligand that may be used with an embodiment of the present invention.

FIG. 6 schematically illustrates an example of a ligand that may be used with an embodiment of the present invention. The ligand may be an antibody having a fragment crystallization (Fc) region 460 and fragment antigen binding (Fab) regions 472. Fab regions 472 may be the antigen binding regions of the antibody that include a variable light region 464 and a constant light region 466, along with a variable heavy region 468 and a constant heavy region 470. Biological activity of antibodies may be determined to a large extent by the Fc region 460 of the antibody molecule. Fc region 460 may include complement activation constant heavy chains 482 and macrophage binding constant heavy chains 484. Fc region 460 and Fab regions 472 may be connected by several disulfide linkages 462. Ligands that do not include the Fc region 460 may be preferable in order to avoid immunogenic response. Examples of these ligands may include antibody fragments, fragment antigen binding fragments (Fabs) 472, disulfide-stabilized variable region fragments (dsFVs) 474, single chain variable region fragments (scFVs) 480, recombinant single chain antibody fragments, and peptides.

An antigen binding fragment (Fab) 472 may include a single Fab region 472 of an antibody. Single Fab region 472 may include a variable light 464 and a constant light region 466 bound to a variable heavy 468 and a constant heavy region 470 by a disulfide bond 462. A disulfide-stabilized variable region fragment (dsFV) 474 may include a variable heavy region 468 and a variable light region 464 of antibody joined by a disulfide bond. A leader sequence 476, which may be a peptide, may be linked to a variable light region 464 and variable heavy regions 468. Single chain variable region fragment (scFV) 480 may include a variable heavy region 468 and variable light region 464 of antibody joined by a linker peptide 478. A leader sequence 476 may be linked to the variable heavy region 468.

Examples of ligand embodiments of the present invention may include, for example, polyclonal antibodies, monoclonal antibodies, chimeric antibodies, humanized antibodies, human antibodies, recombinant antibodies, bispecific antibodies, antibody fragments, scFVs 480, Fabs 472, dsFVs 474, recombinant single chain antibody fragments, peptides, and the like. Bispecific antibodies are non-natural antibodies that bind two different epitopes that are typically chosen on two different antigens. A bispecific antibody is typically comprised of two different fragment antigen binding regions (Fabs) 472. A bispecific antibody may be formed by cleaving an antibody into two halves by cleaving disulfide linkages 462 in Fc region 482 only. Two antibody halves with different Fab regions 472 are then combined to form a bispecific antibody with the typical "Y" structure. One or more ligands can be present in the bioprobe formulation. Antibodies of varying origin may be used according to this embodiment, provided they bind the target, although human, chimeric, and humanized antibodies may aid in avoiding the patient's immunogenic response.

The choice of a marker (antigen) is useful in therapy utilizing bioprobes. For breast cancer and its metastases, a specific marker or markers may be chosen from cell surface markers such as, for example, members of the MUC-type mucin family, an epithelial growth factor (EGFR) receptor, a carcinoembryonic antigen (CEA), a human carcinoma antigen, a vascular endothelial growth factor (VEGF) antigen, a melanoma antigen (MAGE) gene, family antigen, a T/Tn antigen, a hormone receptor, growth factor receptors, a cluster designation/differentiation (CD) antigen, a tumor suppressor gene, a cell cycle regulator, an oncogene, an oncogene receptor, a proliferation marker, an adhesion molecule, a proteinase involved in degradation of extracellular matrix, a malignant transformation related factor, an apoptosis related factor, a human carcinoma antigen, glycoprotein antigens, DF3, 4F2, MGFM antigens, breast tumor antigen CA 15-3, calponin, cathepsin, CD 31 antigen, proliferating cell nuclear antigen 10 (PC 10), and pS2.

For other forms of cancer and their metastases, a specific marker or markers may be selected from cell surface markers such as, for example, vascular endothelial growth factor receptor (VEGFR) family, a member of carcinoembryonic antigen (CEA) family, a type of anti-idiotypic mAB, a type of ganglioside mimic, a member of cluster designation/differentiation antigens, a member of epidermal growth factor receptor (EGFR) family, a type of a cellular adhesion molecule, a member of MUC-type mucin family, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a T/Tn antigen, a hormone receptor, a tumor suppressor gene antigen, a cell cycle regulator antigen, an oncogene antigen, an oncogene receptor antigen, a proliferation marker, a proteinase involved in degradation of extracellular matrix, a malignant transformation related factor, an apoptosis-related factor, and a type of human carcinoma antigen.

In one embodiment of the present invention, the bioprobe attaches to, or associates with, cancer cells and is exposed to the AMF. Heat that is generated will destroy or otherwise deactivate immediately or over time (e.g., apoptosis) the cancer cells, which will be absorbed or otherwise removed from the body. In addition, cells that die by apoptosis will express and release heat shock proteins, such as HSP70, the presence of which can stimulate an immune reaction against any remaining cancer cells. Such a stimulated immune response may serve to protect the individual from future developments of cancer.

In another embodiment, ligand 340 (FIG. 5A) may be targeted to a predetermined target associated with a disease of the patient's immune system. The particular target and ligand 340 may be specific to, but not limited to, the type of the immune disease. Ligand 340 may have an affinity for a cell marker or markers of interest. The marker or markers may be selected such that they represent a viable target on T cells or B cells of the patient's immune system. The ligand 340 may have an affinity for a target associated with a disease of the patient's immune system such as, for example, a protein, a cytokine, a chemokine, an infectious organism, and the like.

In another embodiment, ligand 340 may be targeted to a predetermined target associated with a pathogen-borne condition. The particular target and ligand 340 may be specific to, but not limited to, the type of the pathogen-borne condition. A pathogen is defined as any disease-producing agent such as, for example, a bacterium, a virus, a microorganism, a fungus, and a parasite. Ligand 340 may have an affinity for the pathogen or pathogen associated matter. Ligand 340 may have an affinity for a cell marker or markers associated with a pathogen-borne condition. The marker or markers may be selected such that they represent a viable target on infected cells.

For a pathogen-borne condition, ligand 340 may be selected to target the pathogen itself. For a bacterial condition, a predetermined target may be the bacteria itself, for example, *Escherichia coli* or *Bacillus anthracis*. For a viral condition, a predetermined target may be the virus itself, for example, Cytomegalovirus (CMV), Epstein-Barr virus (EBV), a hepatitis virus, such as Hepatitis B virus, human immunodeficiency virus, such as HIV, HIV-1, or HIV-2, or a herpes virus, such as Herpes virus 6. For a parasitic condition, a predetermined target may be the parasite itself, for example, *Trypanasoma cruzi*, Kinetoplastid, *Schistosoma mansoni, Schistosoma japonicum* or *Schistosoma brucei*. For a fungal condition, a predetermined target may be the fungus itself, for example, *Aspergillus, Cryptococcus neoformans* or *Rhizomucor*.

In another embodiment, the ligand 340 may be targeted to a predetermined target associated with an undesirable target. The particular target and ligand 340 may be specific to, but not limited to, the type of the undesirable target. An undesirable target is a target that may be associated with a disease or an undesirable condition, but also present in the normal condition. For example, the target may be present at elevated concentrations or otherwise be altered in the disease or undesirable state. Ligand 340 may have an affinity for the undesirable target or for biological molecular pathways related to the undesirable target. Ligand 340 may have an affinity for a cell marker or markers associated with the undesirable target.

For an undesirable target, the choice of a predetermined target may be important to therapy utilizing bioprobes. Ligand 340 may be selected to target biological matter associated with a disease or undesirable condition. For arteriosclerosis, a predetermined target may be, for example, apolipoprotein B on low density lipoprotein (LDL). For obesity, a predetermined marker or markers may be chosen from cell surface markers such as, for example, one of gastric inhibitory polypeptide receptor and CD36 antigen. Another undesirable predetermined target may be clotted blood.

In another embodiment, ligand 340 may be targeted to a predetermined target associated with a reaction to an organ transplanted into the patient. The particular target and ligand 340 may be specific to, but not limited to, the type of organ transplant. Ligand 340 may have an affinity for a biological molecule associated with a reaction to an organ transplant. Ligand 340 may have an affinity for a cell marker or markers associated with a reaction to an organ transplant. The marker or markers may be selected such that they represent a viable target on T cells or B cells of the patient's immune system.

In another embodiment, ligand 340 may be targeted to a predetermined target associated with a toxin in the patient. A toxin is defined as any poison produced by an organism including, but not limited to, bacterial toxins, plant toxins, insect toxin, animal toxins, and man-made toxins. The particular target and ligand 340 may be specific to, but not limited to, the type of toxin. Ligand 340 may have an affinity for the toxin or a biological molecule associated with a reaction to the toxin. Ligand 340 may have an affinity for a cell marker or markers associated with a reaction to the toxin.

In another embodiment, ligand 340 may be targeted to a predetermined target associated with a hormone-related disease. The particular target and ligand 340 may be specific to, but not limited to, a particular hormone disease. Ligand 340 may have an affinity for a hormone or a biological molecule associated with the hormone pathway. Ligand 340 may have an affinity for a cell marker or markers associated with the hormone disease.

In another embodiment, the ligand 340 may be targeted to a predetermined target associated with non-cancerous diseased tissue. The particular target and ligand 340 may be specific to, but not limited to, a particular non-cancerous diseased tissue, such as non-cancerous diseased deposits and precursor deposits. Ligand 340 may have an affinity for a biological molecule associated with the non-cancerous diseased tissue.

Ligand 340 may have an affinity for a cell marker or markers associated with the non-cancerous diseased tissue.

In another embodiment, the ligand 340 may be targeted to a proteinaceous pathogen. The particular target and ligand 340 may be specific to, but not limited to, a particular proteinaceous pathogen. Ligand 340 may have an affinity for a proteinaceous pathogen or a biological molecule associated with the proteinaceous pathogen. Ligand 340 may have an affinity for a cell marker or markers associated with the proteinaceous pathogen. For prion diseases, also known as transmissible spongiform encephalopathies, a predetermined target may be, for example, Prion protein 3F4.

Some exemplary embodiments of the bioprobe system, along with associated indications for which they may be utilized, are listed in Table I.

TABLE I

BIOPROBE SYSTEMS AND INDICATIONS

| BIOPROBE SYSTEM | | | |
|---|---|---|---|
| TARGET | MARKER | LIGAND | INDICATION |
| Endothelial cells of growing blood vessels of metastatic cancer cells | Integrin $\alpha v \beta 3$ | Ber EP4 antibody LM609 antibody Integrin antagonist | Metastatic breast cancer, metastatic colon carcinoma |
| Cancer cells | Unglycosylated DF3 antigen | Anti-DF3 antibody | Breast cancer |
| Cancer cells | Kallikreins | Anti-kallikrein antibody | Ovarian and prostate cancer |

TABLE I-continued

BIOPROBE SYSTEMS AND INDICATIONS

BIOPROBE SYSTEM

| TARGET | MARKER | LIGAND | INDICATION |
|---|---|---|---|
| Cancer cells | ErbB2 (HER-2/neu) | Anti-ErbB2 antibody, and scFv (F5), IDM-1 (aka MDX-210) variants | Breast and ovarian cancers |
| Cancer cells | Prostate specific membrane antigen (PSMA) | MDX-070 and 7E11-C5.3 antibodies | Prostate cancer |
| MCF-7 breast cancer cells | 43 Kd membrane associated glycoprotein | 323/A3 antibody | Breast cancer |
| Receptor tyrosine kinases--<br>FLT1<br>FLK1 | Vascular endothelial growth factor (VEGF) and VEGFB and placental growth factor receptors (PGFR) | Anti-FLT1 antibody<br>Anti-FLK1 antibody<br>2C3 antibody | Tumour angiogenesis<br>Tumour angiogenesis |
| Metastatic cancer cells | CAR (coxsackie adenovirus cell-surface receptor) | Anti-CAR antibody | Metastatic prostate cancer |
| Vascular smooth muscle cells of cancer cells | Urokinase type plasminogen activator receptor (uPAR) | Urokinase type plasminogen activator (uPA) | Cancer |
| Blood vessels of cancer cells | Plasminogen activator inhibitor 1(PAI-1) | Anti-PAI-1 antibody | Breast cancer |
| Epithelial ovarian tumour cells | Matrix metaloproteinase 9 (MMP-9) | Anti-MMP-9 antibody | Ovarian carcinomas with lymph node metastasis. |
| Cancer cells | Cyclin A | Anti-cyclin A antibody | Squamous cell carcinoma of the tongue |
| Cancer cells | Cyclin D | Anti-cyclin D(1, 2, 3) antibody | Malignant breast cancer, head and neck squamous cell carcinomas, mantle cell carcinomas, laryngeal squamous cell carcinomas |
| Kidney cortex tissue | Cyclin E | Anti-cyclin E antibody | Human renal cell carcinoma |
| Tumorigenic human breast epithelial cells | Cyclin E | Anti-cyclin E antibody | Breast cancer |
| Malignant epithelial bladder tissue | Cyclin E | Anti-cyclin E antibody | Transitional cell carcinoma of the urinary bladder |
| Cancer cells | Cdc 2 | Anti-cdc 2 antibody | Breast cancer |
| Malignant epithelial bladder tissue | P27 | Anti-phospho p27 antibody | Transitional cell carcinoma of the urinary bladder |
| Cancer cells | P73 | Anti-p73 antibody | Lung carcinogenesis, bladder carcinogenesis, neuroblastoma, breast cancer |
| Cancer cells | Ras | Anti-ras antibody | Breast cancer |
| Cancer cells | c-myc | Anti C-myc antibody | Breast cancer |
| Cancer cells | c-fms | Anti-c-fms antibody | Breast cancer |
| Cancer cells | Hepatocyte growth factor receptor (HGFR) | Anti-HGFR antibody | Colorectal cancer |
| Cancer cells | c-met | Anti-c-met antibody | Gastric and colon cancers, hepatomas, ovarian cancer, skin cancer |
| Large granular lymphocyte (LGL) leukaemia cells | Apoptosis related factors:<br>Fas<br>FasL | Anti-CD95 (Fas) antibody | Leukaemia, prostate cancer |
| Cancer cells | Non-receptor protein tyrosine kinase V-Src and C-Src | Anti c-src-polyclonal antibody | Metastatic colorectal cancer, and late stage breast cancer |

TABLE I-continued

BIOPROBE SYSTEMS AND INDICATIONS

BIOPROBE SYSTEM

| TARGET | MARKER | LIGAND | INDICATION |
|---|---|---|---|
| Cancer cell | CAR (coxsackie Adenovirus cell-surface receptor) | Onyx-015 adenovirus | Lung, ovarian, other cancers |
| Cancer cell | Epidermal growth factor receptor (EGFR) | Molecule 225 antibody | Cancer |
| Cancer cells | D6 antigen | Anti-D6 antibody | Vascular tumours including Kaposi's sarcoma |
| Cancer cells | 2C4 antigen | Anti-2C4 antibody | Breast, prostate, other cancers |
| Cancer cells | Cytokeratin epithelial marker and/or telomerase reverse transcriptase | S5A10-2 antibody | Non-small cell lung cancer |
| Cancer cells | Carcinoembryonic Antigen (CEA) | MFE-23 scFv of anti-CEA antibody | Colorectal cancer |
| Cancer cells | Proliferating cell nuclear antigen (PCNA) | Anti-PCNA antibody | Breast cancer |
| Cancer cells | Neu 3, a membrane associated sialidase | Anti-neu 3 sialidase antibody | Colon cancer |
| Cancer cells | P13KC2 beta (cancer cell signal mediator) | Anti-P13KC2beta antibody | Lung cancer |
| Cancer cells | Guanylyl cyclase-C (GC-C) receptor | Anti-GC-C antibody | Esophageal or gastric cancer |
| Cancer cells | Transforming growth factor beta (TGFB) receptor | Anti-TGFB antibody | Breast cancer |
| Cancer cells | Platelet derived growth factor receptor (PDGFR) PDGFR-A (alpha) PDGFR-B (beta) | Anti-PDGF-A antibody Anti-PDGF-B antibody | Lung cancer Bone cancer |
| Cancer cells and blood vessels | Vascular endothelial growth factors VEGFR Angiopoietin | Tie1 Tie2 | Cancer Cancer |
| Cancer cells | Mucin family of receptors | Anti-MUC-1 antibody, 12E antibody 3D antibody AS antibody | Colorectal and ovarian carcinomas |
| Cancer cells | TAG-72 | B72.3 antibody | Breast and lung cancers |
| Cancer cells | Human milk fat globule receptor | NCL-HMFG1 and NCL-HMFG2 antibodies | Breast, lung, colon, and prostate cancers |
| Methionine synthase and L-methylmalonyl-CoA mutase | Cobalamin receptor | B12 (riboflavin, and variants) cobalamin and variants such as adenosylcobalamin transcobalamin | Breast, lung, colon, sarcomatous thyroid or central nervous system maliqnancies cancer |
| Cancer cells | Glioma chloride channel | Scorpion toxin-chlorotoxin and chlorotoxin-like molecules | Gliomas |
| Cancer cells | 40 kD glycoprotein antiqen | NR-LU-10 antibody | Small cell lung cancer |
| CNS cells and tissue | Brain-specific chondroitin sulphate proteoglycan Brain enriched hyaluronan binding (BEHAB-aka brevican | Anti-BEHAB antibody | Gliomas |
| Cancer cells | Catenins Alpha catenin Beta catenin Gamma catenin | Anti-alpha catenin antibody Anti-beta catenin antibody Anti-gamma catenin antibody | Colorectal carcinoma, non-small cell lung cancer Breast cancer Thyroid cancer |
| Cancer cells | Interleukin (IL) receptors IL13 receptor | IL13-PE38 antibody | Kidney, brain, breast, and head and neck cancers, and Kaposi's sarcoma |

TABLE I-continued

BIOPROBE SYSTEMS AND INDICATIONS

BIOPROBE SYSTEM

| TARGET | MARKER | LIGAND | INDICATION |
|---|---|---|---|
| Cancer cells | Mesothelin receptor | Anti-mesothelin antibody, and SS1(dsFv) variant | Mesotheliomas Ovarian cancer and mesotheliomas |
| Cancer cells | CD44 surface adhesion molecule | Anti-CD44 antibody | Prostate cancer |
| Cancer cells | EGFRvIII | Ua30:2 antibody L8A4 antibody DH8.3 antibody 81C6 antibody | Brain, colorectal, pancreatic, biliary, liver cancers and soft tissue sarcomas. |
| Receptor tyrosine kinases FLT1 | Vascular endothelial growth factor (VEGF) and VEGFB | Anti-FLT1 antibody | Atherosclerotic plaques |
| Smooth muscle cells in the lumen of blood vessels | Basic fibroblast growth factor receptor (bFGFR) | Anti-bFGF antibody | Restenosis |
| Vulnerable plaque | Oxidized low density lipoprotein (OxLDL) | Oxidation-specific antibodies (Ox-AB) MDA-2 antibody | Atherosclerosis and vascular disease |
| Vulnerable plaque | Malondialdehyde-modified LDL (MDA-LDL) | 1K17 antibody | Atherosclerosis and vascular disease |
| *M. Tuberculosis* bacilli | APA-antigen | Anti-APA antibody | Tuberculosis |
| Retrovirus infected cells | TGFA (alpha) | Anti-TGFA antibody | HIV |
| Leukocytes | Alpha4 subunit of alpha4beta1-integrin (VLA-4) and alpha4beta7-integrin | Antegren | Multiple sclerosis |
| Receptor tyrosine kinases FLT1 | Vascular endothelial growth factor (VEGF) and VEGFB | Anti-FLT1 antibody | Autoimmune joint destruction (arthritis, lupus, etc) |
| Plasmodium falciparum | Apical membrane antigen-1 (AMA-1) | Anti-AMA-1 antibody | Malaria |
| Cells of the immune system | CD30 | AC10, HeFil, and derivatives of AC10 and HeFil | Immunological disorders other than cancer |
| Hepatitis C virus | Hepatitis C virus core protein | 19D9D6 Monoclonal Antibody | Hepatitis C infection |
| Tumor vascular cells | Vascular endothelial growth factor (VEGF) | MV833 and HuMV833 antibodies | Cancer |
| Tumor cells | Cytokeratin | Anti-cytokeratin AE1/3 and anti-CAM5.2 antibodies | Epitheleoid sarcomas |
| Tumor cells | Thomsen Friedenreich (TF) antigen | M170, chimeric M170, MaB 170H.82R1808 | Breast, Prostate, Ovarian, and Lung cancers |
| Tumor cells | CEA | HumaSpect ™, Votumumab, Mab 88BV59 | Colon and Ovarian cancers |
| Tumor cells | EFG-r | ABX-EGF | Colon, NSCLC, Prostate, and Renal cancers |
| Tumor cells | EGF-r | HuMax-EGFr | Head, Neck, Breast, Colon, Prostate, Lung, and Ovarian cancers |
| Tumor cells | EGF-r | TheraCIM ™, h-R3 | Head and Neck cancers |
| Tumor cells | CEA | KSB309 ™ | Oral cavity, and Pharngial cancers |
| Tumor cells | CEA | 4B5-H | Melanoma |
| Tumor cells | GD2 ganglioside | ABX-MA1 | Melanoma, Neuroblastoma, NSCLC |
| Tumor cells | CTLA4; CD152 | MDX-010 | Melanoma |
| Tumor cells | GD2 ganglioside | TriGem, Mab-1A7 | Melanoma |
| Tumor cells | CA125; MUC-16 | ACA-125 | Ovarian cancer |
| Tumor cells | Polymorphic epithelial mucin | R1549, Pemtumomab, MuHMFg1, HuHMFg1 | Ovarian, Stomach, Breast, Lung, and Prostate cancers |
| Tumor cells | CA125 | OvaRex ™, Mab-B42.13, Ov | Ovarian cancer |

TABLE I-continued

BIOPROBE SYSTEMS AND INDICATIONS

BIOPROBE SYSTEM

| TARGET | MARKER | LIGAND | INDICATION |
|---|---|---|---|
| Tumor cells | | VB2-011, H-ll ScFv, Novo Mab-G2ScFv | Breast, Ovarian, and Colorectal cancers |
| Tumor cells | CEA | CEA-Cide, Labetuzumab | Breast, Colon, and Lung cancers |
| Tumor cells | VEGF | Avastin ™, Bevacizumab, rhuMAb-VEGF | Breast, Colorectal, NSCLC, and Renal cancers |
| Tumor cells | LewisY Ag | SGN-15, CBR96 | Breast, NSCLC, and Ovarian cancers |
| Tumor cells | HER2 | OmniTag ™, Pertuzumab, rhuMAb 2C4 | Breast, Ovarian, Lung, and Prostate cancers |
| Tumor cells | MUC1 | BrevaRex ™, Mab AR20.5 | Breast, Ovarian, and Multiple Myeloma cancer |
| Tumor cells | MUC1 | Therex ™, R1550, HuHMFGl | Breast, Ovarian, Pancreatic, and Gastric cancers |
| Tumor cells | Ep-CAM | ING-1 | Breast, Lung, Prostate, and Pancreatic cancers |
| Tumor cells | $\alpha v \beta 3$ integrin | Vitaxin ™, huLM609 | Solid tumors |
| Tumor cells | $\alpha v \beta 3$ integrin | Mab-MEDI-522, huLM609 | Advanced solid tumors |

Figure 5B:
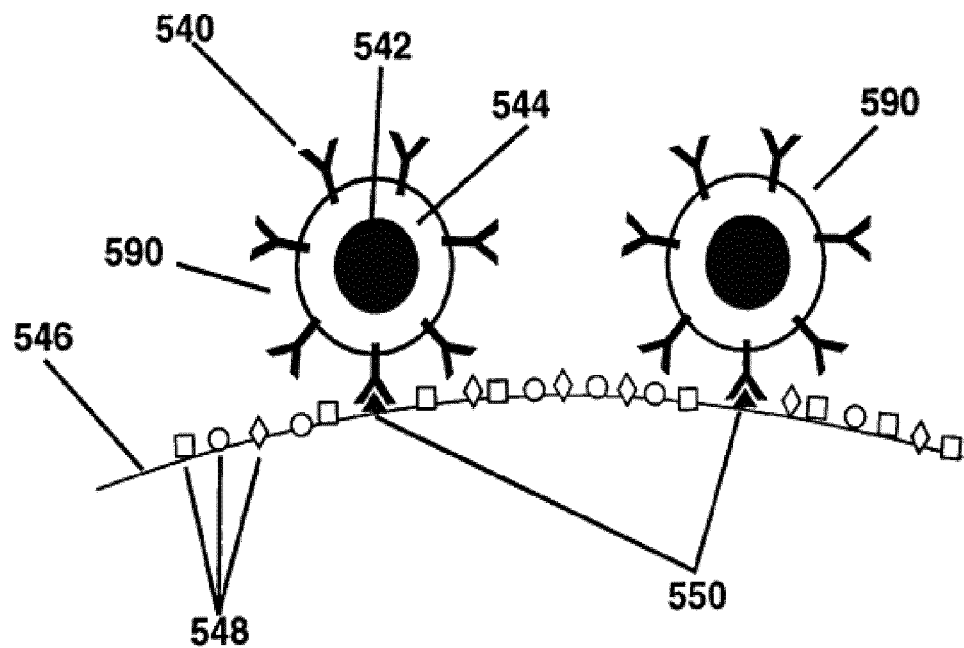
FIG. 5B illustrates an embodiment of the present invention wherein a bioprobe, comprising a susceptor, which comprises a coating, is attached to or associated with a target (such as a cell) by one or more targeting ligands.

FIG. 5B illustrates an embodiment of the present invention wherein a bioprobe 590, comprising a susceptor 542, which comprises a coating 544, is attached to or associated with a target (such as a cell) 546 by one or more targeting ligands 540. Cell 546 may express several types of markers 548 and 550. The specificity of bioprobe 590 is represented by its attachment to targeted marker 550 over the many other markers or molecules 548 on cell 546. One or more bioprobes 590 may attach to or associate with cell 546 using ligand 540. Ligand 540 may be adapted and bioprobe 590 may be designed such that bioprobe 590 remains externally on cell 546 or may be internalized into cell 546. Once bound to cell 546, the susceptor 542 is energized in response to the energy absorbed. For example, the susceptor 542 may heat up in response to the energy absorbed. The heat may pass through coating 544 or through interstitial regions to the cell 546, for example by convection, conduction, radiation, or a combination of these heat transfer mechanisms. The heated cell 546 becomes damaged, preferably in a manner that causes irreparable damage. When bioprobe 590 becomes internalized within cell 546, bioprobe 590 may heat cell 546 internally via convection, conduction, radiation, or a combination of these heat transfer mechanisms. When a sufficient amount of energy is transferred by bioprobe 590 to cell 546, cell 546 dies via necrosis, apoptosis, or another mechanism.

A method of administering bioprobes 590 to the desired area for treatment and the dosage may depend upon, but is not limited to, the type and location of the diseased material. The size range of bioprobes 590 allows for microfiltration for sterilization. An administration method may be, for example, wash, lavage, as a rinse with sponge, or other surgical cloth as a perisurgical administration technique. Other methods of administration include intravascular injection, intravenous injection, intraperitoneal injection, subcutaneous injection, and intramuscular injection. Bioprobes 590 may be formulated in an injectable format (suspension, emulsion) in a medium such as, for example, water, saline, Ringer's solution, dextrose, albumin solution, or oils. Bioprobes 590 may also be administered to the patient through topical application via a salve or lotion, transdermally through a patch, orally ingested as a pill or capsule or suspended in a liquid, or rectally inserted in suppository form. Bioprobes 590 may also be suspended in an aerosol or pre-aerosol formulation suitable for inhalation via the mouth or nose. Once administered to the patient, delivery of bioprobes 590 to the target site may be assisted by an applied static magnetic field due to the magnetic nature of the bioprobes. Assisted delivery may depend on the location of the target.

A magnetic body is divided into uniformly magnetized regions (domains) separated by domain walls (Bloch walls) in order to minimize its magnetostatic energy. This type of magnetic structure is referred to as a multidomain structure. The energy to be minimized is the total energy, which is a sum of the magnetostatic, the exchange, and the anisotropy energies as well as the energy of the domain wall itself. Therefore, it is the final balance of energies that determines the domain structure and shape.

When the dimensions of the magnetic body, i.e. crystal, are reduced, the size of the domains is also reduced, and their structure, as well as the width and the structure of the domain walls, may change. Due to the cost of energy wall formation, the balance with the magnetostatic energy limits the subdivision in domains to a certain optimum domain size. Indeed, there is a corresponding lower limit of crystal size, below which only a single-domain structure can exist, since the energy increase due to the formation of domain walls is higher than the energy decrease obtained by dividing the single domain into smaller domains.

For typical magnetic materials, the dimensional limit is in the range of about 20-800 nm, depending on the spontaneous magnetization and on the anisotropy and exchange energies. The change from a multidomain to a single-domain structure is accompanied by a strong increase of the coercive field. Variations of the dimensional limit occur and are governed by material composition, material shape, and crystal properties such as anisotropy and exchange energies. Since material shape and crystal properties are in turn determined by the material processing and environmental conditions, i.e., sample history, it is impossible to categorically state single-domain dimensions for even a material composition. Thus, each sample must be individually characterized to determine the average domain structure.

Superparamagnetic Particles: The anisotropy energy in a single-domain particle is proportional, in a first approximation, to the volume V. For uniaxial anisotropy, the associated energy barrier, separating easy magnetization, directions of the crystal (i.e., the low-energy directions of the magnetization vector, or spin system) is EB=KV. Thus, with decreasing particle size, the anisotropy energy decreases, and for a grain size lower than a characteristic value, it may become so low as to be comparable to or lower than the thermal energy kT. This implies that the energy barrier for magnetization reversal may be overcome, and then the total magnetic moment of the particle can thermally fluctuate, like a single spin in a paramagnetic material. Thus, the entire spin system may be rotated, the spins within the single-domain particles remaining magnetically coupled (ferromagnetically or antiferromagnetically). The magnetic behavior of an assembly of such ultrafine, independent magnetic particles is referred to as superparamagnetism. [For a discussion on superparamagnetism, also refer to J. L. Dormann, "Magnetic Relaxation in Fine-Particle Systems", Advances in Chemical Physics, Vol. XCVIII, ISBN 0-471-16285-X, 1997, Wiley & Sons, Inc., page 283-494.]

Superparamagnetic behavior is exhibited by particles with dimensions in a defined range. If they are too small, almost all the atoms lie on the surface, leading to electronic and magnetic properties strongly modified with respect to the bulk properties, and the superparamagnetic model cannot be applied. This does not mean that no relaxation of the magnetic moment occurs, but the laws governing it are expected to be different. It is difficult to state precisely a lower dimensional limit for superparamagnetic behavior, as it depends on several parameters. In many cases, it is believed to be about 2 nm. As far as the upper limit is concerned, it is given in principle by the characteristic size for a single-domain particle, as long as the single-domain state and structure are effective (some uncertainties remain for some particular cases). Actually the characteristic grain size of a magnetic material for superparamagnetic relaxation depends on the anisotropy constants and magnetic saturation values. As an example, for uniaxial anisotropy and $K=5*10^5$ erg/cm$^3$, for spherical particles this corresponds to a characteristic diameter $\varphi_c \leq 20$ nm.

For fine magnetic particles the actual magnetic behavior depends not only upon the material and physical characteristics of the particles, but also on the value of the measuring time ($\tau_m$) of the specific experimental technique with respect to the relation time ($\tau$) associated with overcoming the energy barriers. The characteristic relaxation time, $\tau$, varies exponentially with the EB/kT ratio. If $\tau_m \gg \tau$, the relaxation appears to be so fast that a time average of the magnetization orientation is observed in the experimental time window, and the assembly of particles behaves like a paramagnetic system, i.e., superparamagnetic behavior is observed and the sample appears to be in the superparamagnetic state. On the other hand, if $\tau_m \ll \tau$, the relaxation appears so slow that quasi-static properties are observed (blocked state), as with magnetically ordered crystals, although strongly influenced by the particle surface structure.

The blocking temperature $T_B$, separating the two states, is defined as the temperature at which $\tau_m = \tau$. Therefore, $T_B$ is not uniquely defined as well as $\varphi_c$, but is related to the time scale of the experimental technique. As an example, for $Fe_3O_4$ (K=4.4*10$^5$ erg/cm$^3$) at 290 K, the characteristic grain diameter for superparamagnetism, below which superparamagnetic relaxation and above which quasi-static properties are observed, is $\varphi_c \approx 17$ nm for DC susceptibility measurements, while it is $\varphi_c \approx 9$ nm for Mossbauer spectroscopy experiments, having a much shorter measuring time.

The blocking temperature $T_B$ for a magnetic particle increases with increasing size and for a given size increases with decreasing measuring time, and then the observation of a superparamagnetic of blocked state depends on the experimental technique. The highest value of TB is represented by the Curie (or Neel) temperature, at which the transition from the superparamagnetic to the paramagnetic state occurs. For magnetite, this is about 858 K. The techniques currently used to study the superparamagnetic relaxation are DC susceptibility, AC susceptibility, Mossbauer spectroscopy, ferromagnetic resonance, and neutron diffraction. Table II displays the time window associated with each measurement technique.

TABLE II

TECHNIQUES TYPICALLY USED TO MEASURE MAGNETIC PROPERTIES OF ULTRAFINE PARTICLES, AND THEIR TIME WINDOWS

| Technique | Time window (sec.) | Comments |
|---|---|---|
| DC susceptibility | 100 | Estimated, time is not well defined. |
| AC susceptibility | $10^2$-$10^4$ $10^{-1}$-$10^{-5}$ $10^{-5}$-$10^{-8}$ | Low frequency Classical experiments Very high frequencies, difficult to realize |
| Mossbauer spectroscopy | $10^{-7}$-$10^{-9}$ | For $^{57}$Fe |
| Ferromagnetic resonance | $10^{-9}$ | |
| Neutron diffraction | $10^{-8}$-$10^{-12}$ | Depends upon type of experiment |

Complexity of Actual Fine-Particle Systems and Hysteretic Heating: The discussion above was restricted to idealized examples of magnetic ultrafine (nanometer-sized) particles. Unfortunately, the actual situation in materials consisting of fine particles is very complex, and it is often necessary to account for the simultaneous presence of different factors.

First, in actual systems, there is always a distribution of particle size. Moreover, different terms can contribute to the total anisotropy energy of a single-domain particle, for example magnetocrystallinity, magnetostatic, shape, stress, and surface. The surface, which is closely related to the detailed chemical nature of surface and grain boundary, may become the dominant contribution to the anisotropy energy for particles smaller than about 10 nm.

For the application considered in this disclosure, a suspension of magnetic nanometer-sized (may be single-domain) particles is surrounded by polymer to form a bioprobe. When this suspension is exposed to an externally applied alternating magnetic field of frequency f and magnitude H, the magnetic moments within each particle may respond by changing orientation to align with the imposed external field. When the field direction is reversed, the magnetic moments of the particles attempt to respond by reorienting with the changing field vector. The extent to which they are able to accomplish this, and the extent to which they must overcome their internal energies (described above) may result in the production of heat. The amount of heat released by the particles will depend upon the several factors governing both the orientation of the particle magnetic moment with respect to its easy axis in the crystal and the external field, shape, anisotropy constant, etc. Thus, application of a magnetic field for hysteretic heating may be considered as a magnetic sampling experiment since it possesses the relevant conditions of time scale and temperature necessary in magnetic characterization experiments (cf. Table I). Typically, the magnetic properties of suspensions of nanoparticles are characterized by techniques with time windows (and temperatures) that do not correspond to the conditions of the actual application for hysteretic heating. This discrepancy may lead to the mis-characterization of the particle as being superparamagnetic, as this is the behavior observed during magnetic characterization. But this characterization may not be consistent for the application because the conditions (temperature, time scale) employed during application may be very different, with the particles exhibiting blocked (or ferromagnetic) behavior. Thus, to characterize actual samples with the inherent variations of particle size, shape, magnetic crystalline energies, etc. based upon measurement conditions that do not correspond to conditions actually used for hysteretic heating may be erroneous.

Biomineralization and Magnetic Nanoparticles: Two fundamentally different modes of biomineralization can produce magnetic nanometer-sized particles. One is referred to as biologically induced mineralization (BIM), in which an organism modifies its local microenvironment creating conditions suitable for the chemical precipitation of extracellular mineral phases. The second mode is referred to as boundary organized biomineralization (BOB), in which inorganic particles are grown within or on some organic matrix produced by the organism.

Bacteria that produce mineral phases by BIM do not strictly control the crystallization process, resulting in particles with no unique morphology and a broad particle size distribution. Non-magnetotactic dissimilatory iron-reducing and sulfate-reducing bacteria produce magnetite, siderite, vivianite, and iron sulfides by BIM processes. For example, the iron-reducing bacterium Geobacter metallireducens (formerly GS-15) is a non-magnetotactic anaerobe that couples the oxidation of organic matter to the reduction of ferric iron, inducing the extracellular precipitation of fine-grained magnetite as a byproduct.

In contrast to BIM, bacteria that produce mineral phases by a BOB processes exert strict control over size, morphology, composition, position, and crystallographic orientation of the particles. One example of microorganisms using BOB process to produce iron biominerals is magnetotactic bacteria. These bacteria synthesize intracellular, membrane-bounded $Fe_3O_4$ (magnetite), $Fe_3S_4$ (possible $Fe_7S_8$) and $FeS_2$ particles called manetosomes. Various arrangements of magnetosomes within cells impart a permanent magnetic dipole moment to the cell, which effectively makes each cell a self-propelled biomagnetic compass.

The hallmarks of magnetosomes are their size specificity and distinctive crystal morphologies. Many magnetosomes fall within a size of about 35-120 nm when measured along their long axis. This size specificity of magnetosomes is significant because within this size range the particles are uniformly magnetized, permanent single magnetic domains.

For a given cell type, magnetosomes have a uniform size, shape, crystal morphology, and arrangement within the cell. Magnetosomes occur in at least three different crystal forms determined using transmission electron microscopy. The simplest form, found in Magnetospirillum magnetotacticum, is cubo-octahedral, which preserves the cubic crystal symmetry of magnetite. A second type, found in coccoid and vibrioid strains, is an elongated hexagonal prism with the axis of elongation parallel to the <111> crystal direction. A third type, observed in some uncultured cells, is an elongated cubo-octahedral form producing unique bullet-shaped, teardrop, and arrowhead particles.

The ability of these bacteria to produce precisely formed, single-domain magnetic particles may be valuable for the production of bioprobes. These cells can be grown in cell cultures to manufacture quantities of magnetic particles, which can then be harvested and further modified with biocompatible coating material and ligands to produce the bioprobes. In addition, molecular biology, gene sequencing and cloning techniques may be used to further modify the strains of bacteria to produce well-controlled single domain particles all with identical sizes and properties that are different from those observed in the natural state.

Figure 7:
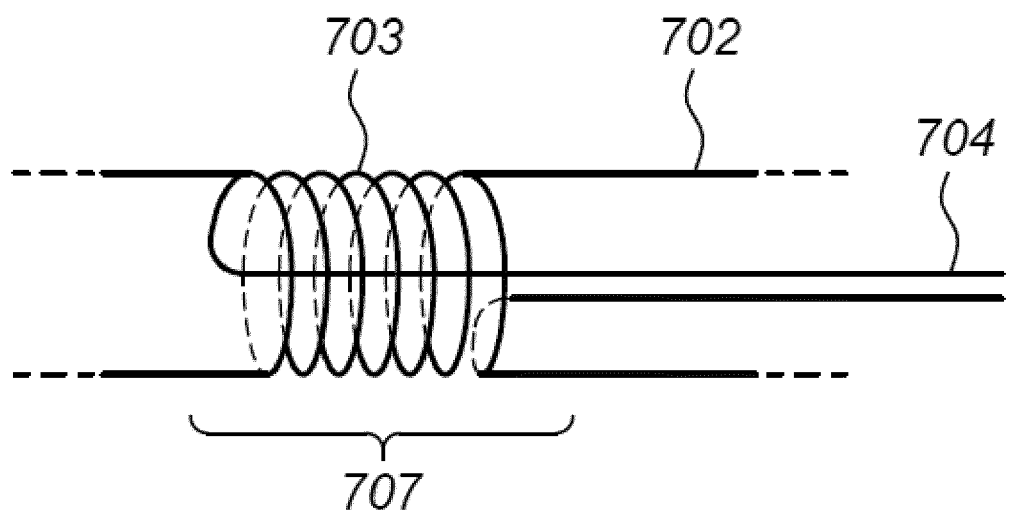
FIGS. 7, 8, and 9 schematically represent embodiments of a portion of the distal end 707, 807, 907 of the catheter shaft 702, 802, 902 according to the present invention.
Figure 8:
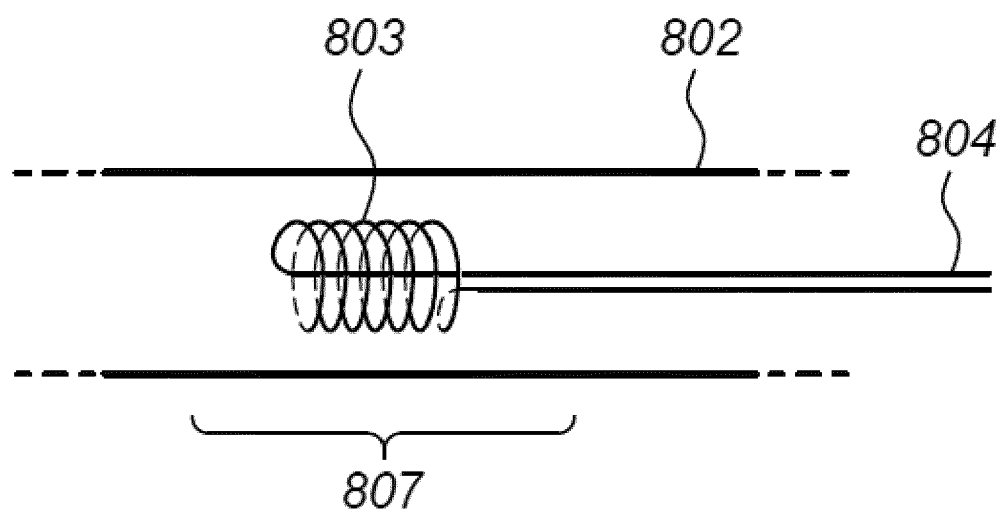
Figure 9:
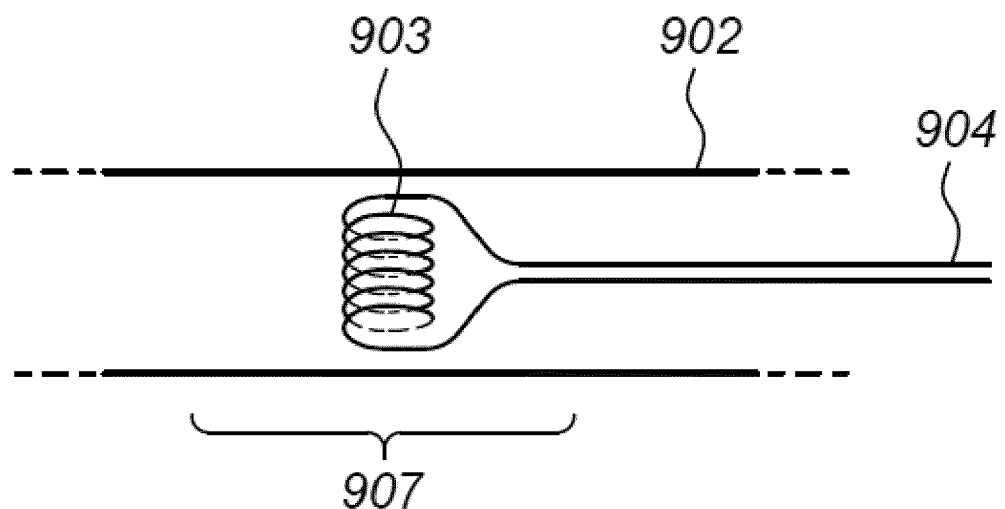

FIGS. 7, 8, and 9 schematically represent embodiments of a portion of the distal end 707, 807, 907 of the catheter shaft 702, 802, 902 according to the present invention, comprising an emitter coil 703, 803, 903 connected to electrical wiring 704, 804, 904 extending from the distal end to the proximal end of the catheter shaft. In FIGS. 7 and 8 the central axis of the emitter coil 703, 803 is substantially parallel to the longitudinal axis of the catheter. In FIG. 9 the central axis of the emitter coil 903 is not substantially parallel to the longitudinal axis of the catheter.

The guidewire or guiding tip can be used to bring the emitter coil of the catheter at a position in a patient's body near the implant device, and preferably surrounded by the implant device, thereby limiting the amount of body tissue in between the emitter and the circumferential structure of the implant device, which comprises one or more pick-up coils. Due to the circumferential nature of the structure, at least one of the pick-up coils of the implant device comprises a central axis. The longitudinal axis of the catheter can be positioned substantially parallel to the central axis of this pick-up coil. When the central axis of the emitter coil is substantially parallel to the longitudinal axis of the catheter, it is also substantially parallel to the central axis of the pick-up coil, which results in a good coupling of the emitter and pick-up coils to transfer time-varying magnetic fields. The amount of emitted electromagnetic radiation lost by absorption in body tissue is hence significantly limited compared to the prior art.

Figure 10:
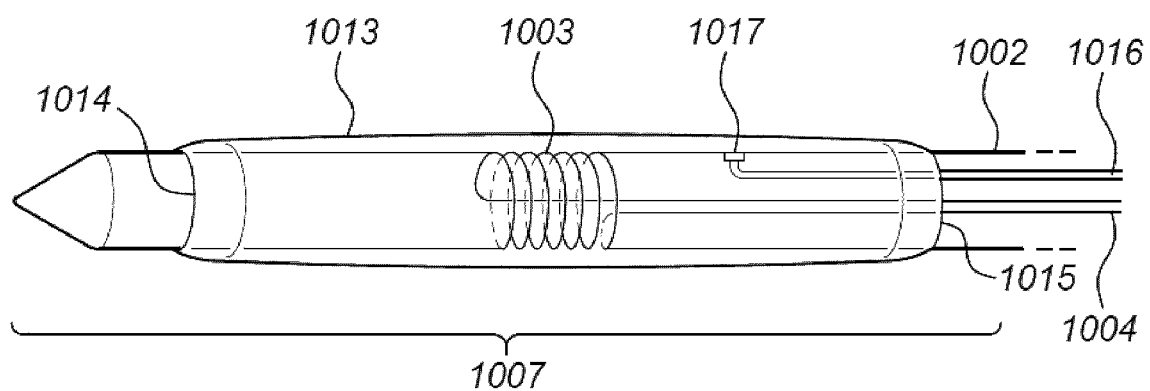
FIGS. 10 and 11 schematically represent embodiments of the distal end of a catheter shaft according to the present invention.
Figure 11:
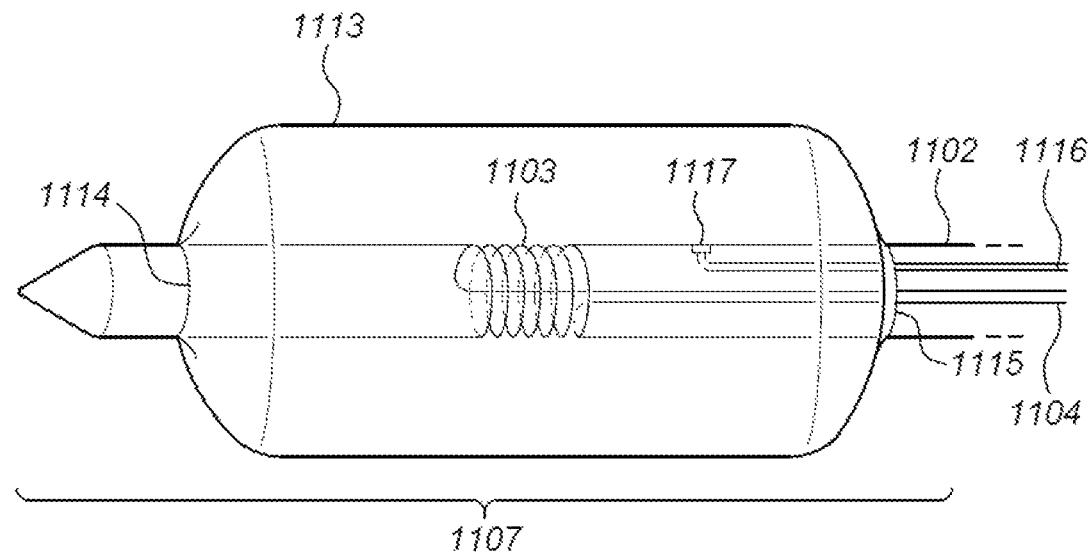

FIGS. 10 and 11 schematically represent embodiments of the distal end 1007, 1107 of a catheter shaft 1002, 1102 according to the present invention comprising a balloon 1013, 1113, whereby the balloon comprises two air-tight connections 1014, 1114 and 1015, 1115 to the catheter shaft. The distal end of an inflation lumen 1016, 1116 is in communication with the interior of the balloon 1013, 1113 by means of an opening 1017, 1117 in the catheter shaft. In FIG. 10 the balloon is not inflated. In FIG. 11 the balloon is inflated.

In a preferred embodiment of the present invention, the balloons are adapted to position upon inflation the catheter shaft at or near the center of a vessel (e.g. a vein) and/or the implant device, preferably by a substantial cylindrical symmetry of the outermost exterior regions of the inflated balloons with respect to the longitudinal axis of the catheter.

Figure 12:
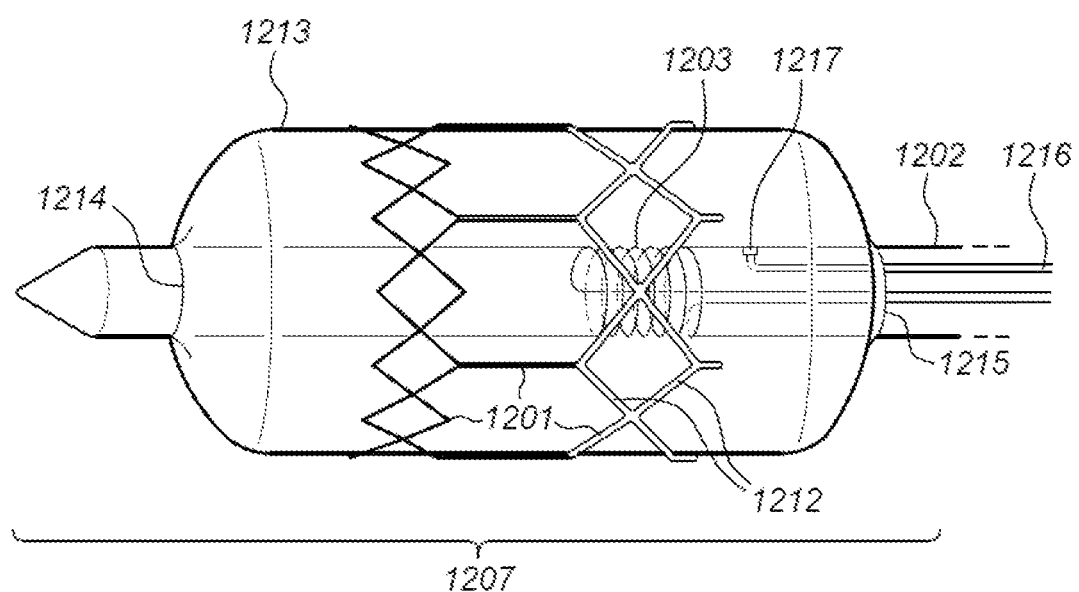
FIGS. 12 and 13 schematically represent embodiments of an implant device according to the present invention and embodiments of the distal end of a catheter shaft according to the present invention.
Figure 13:
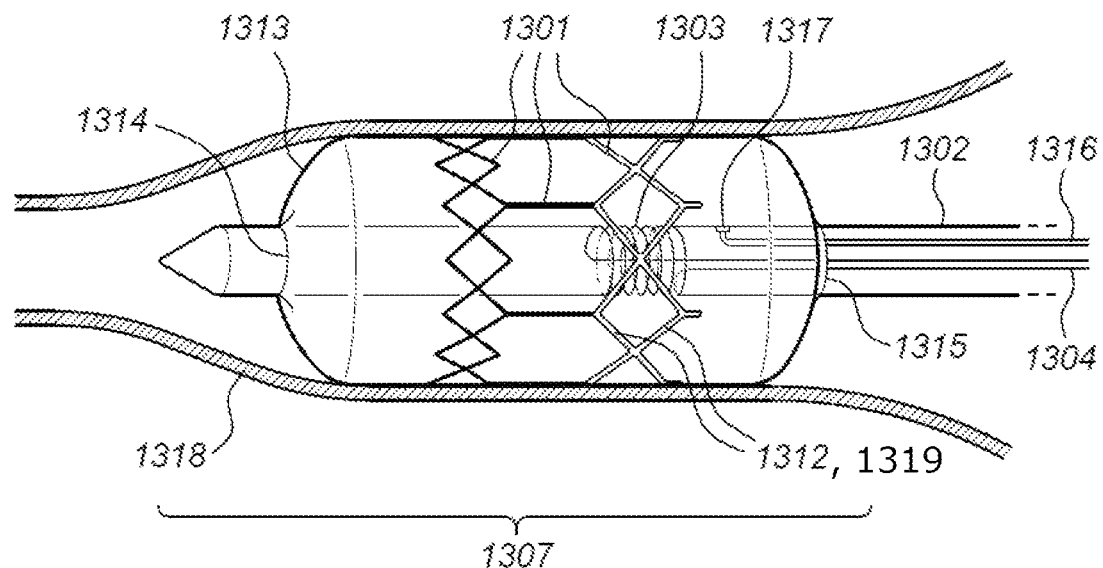

FIGS. 12 and 13 schematically represent embodiments of an implant device 1201, 1301 according to the present invention and embodiments of the distal end 1207, 1307 of a catheter shaft 1202, 1302 according to the present invention comprising a balloon 1213, 1313, whereby the balloon comprises two air-tight connections 1214, 1314 and 1215, 1315 to the catheter shaft. The distal end of an inflation lumen 1216, 1316 is in communication with the interior of the balloon 1213, 1313 by means of an opening 1217, 1317 in the catheter shaft. The outermost exterior region of the inflated balloon 1213, 1313 has cylindrical symmetry with respect to the longitudinal axis of the catheter, thereby aligning central axis of the emitter coil 1203, 1303 coaxially with the central axis of the pick-up coil 1212, 1319 of the implant device 1201, 1301.

The central axes of the emitter and pick-up coils will reach upon inflation of the balloons near perfect coaxial alignment, when the emitter coil of the catheter is at a position in a patient's body near the implant device, and preferably surrounded by the implant device. The near perfect coaxial alignment of the emitter and pick-up coils ensures an even better transfer of time-varying magnetic fields from the emitter coil to the pick-up coil.

In addition, inflation of the balloons adapted for complete circumferential surface contact with the vessel and/or the implant device can stop the flow in the vessel entirely, thereby stopping the drain of heat from the ablation region by forced convection due to the fluid flow.

In an embodiment of the present invention, one of the balloons is adapted to thermally insulate the ablation region from fluid in the vessel, e.g. blood in the vein, upon inflation of the balloon.

In FIG. 13 the inflated balloon 1313 is in complete circumferential surface contact with the implant device 1301 as well as the vessel 1318. The ablation region 1312 is thereby thermally insulated from fluid in the vessel, e.g. from blood in the vein.

In an embodiment of the present invention, at least one of the balloons is a perfusion balloon.

Figure 14:
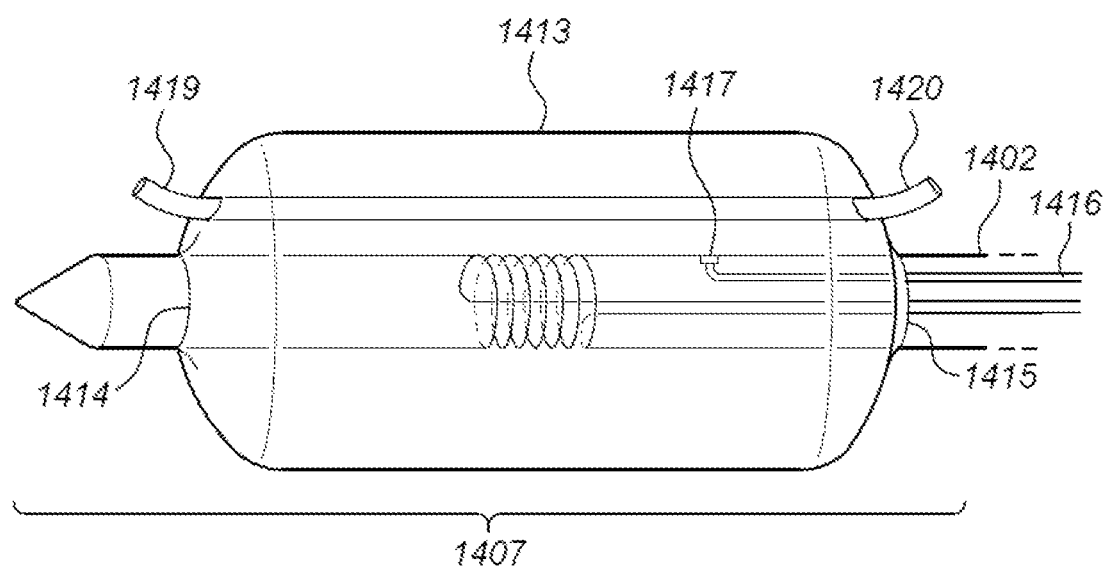
FIGS. 14 and 15 schematically represent embodiments of the distal end of a catheter shaft according to the present invention.
Figure 15:
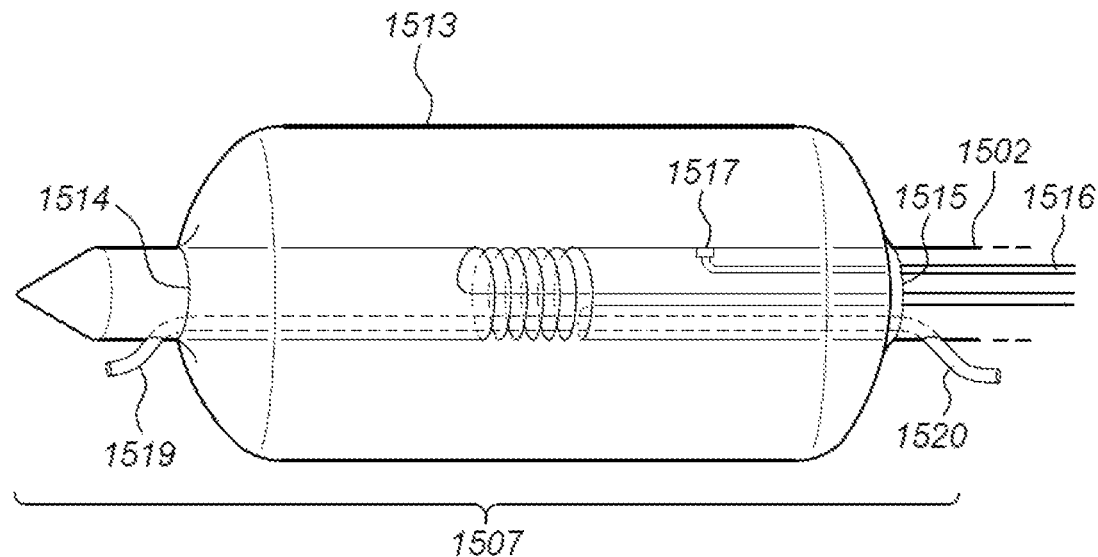

FIGS. 14 and 15 schematically represent embodiments of the distal end 1407, 1507 of a catheter shaft 1402, 1502 according to the present invention comprising a balloon 1413, 1513, whereby the balloon comprises two air-tight connections 1414, 1514 and 1415, 1515 to the catheter shaft. The balloon 1413 in FIG. 14 comprises a perfusion channel with two ends 1419 and 1420, which can allow limited flow through the vessel, e.g. blood flow in a vein, even if the outermost exterior region of the inflated balloon is in complete circumferential surface contact with the implant device and/or the vessel to insulate the ablation region from the blood. The perfusion channel in the balloon 1413 in FIG. 14 comprises a tube. The perfusion channel in the balloon can also comprise a lumen comprising a wall of essentially the same material and thickness as the outermost wall of the balloon. A perfusion balloon is a term denoting a balloon comprising a perfusion channel. FIG. 15 schematically represents an embodiment of the present invention, in which the catheter shaft comprises a perfusion channel with two ends 1519 and 1520.

In an embodiment of the present invention, one or more balloons are coated with an anticoagulant, preferably heparin sulphate.

By thermally insulating the ablation region from the fluid flow with an inflated balloon, the drain of heat from the ablation region by forced and/or natural convection is removed. With a perfusion balloon, limited fluid flow can still be sustained, thereby significantly diminishing the chance of clots, e.g. blood clots. Coating the balloons with an anticoagulant can also significantly diminish the chance of e.g. blood clots.

In an embodiment of the present invention, the longitudinal body of the catheter comprises an additional transfer lumen 1416, 1516 with a distal end and a proximal end, and the distal end of the transfer lumen is in communication with the exterior region of the balloons via one or more openings 1417, 1517 in the catheter shaft at or near the distal end of the catheter, and the proximal end of the transfer lumen is adapted for connection with a fluid delivery and/or drainage system.

Figure 16:
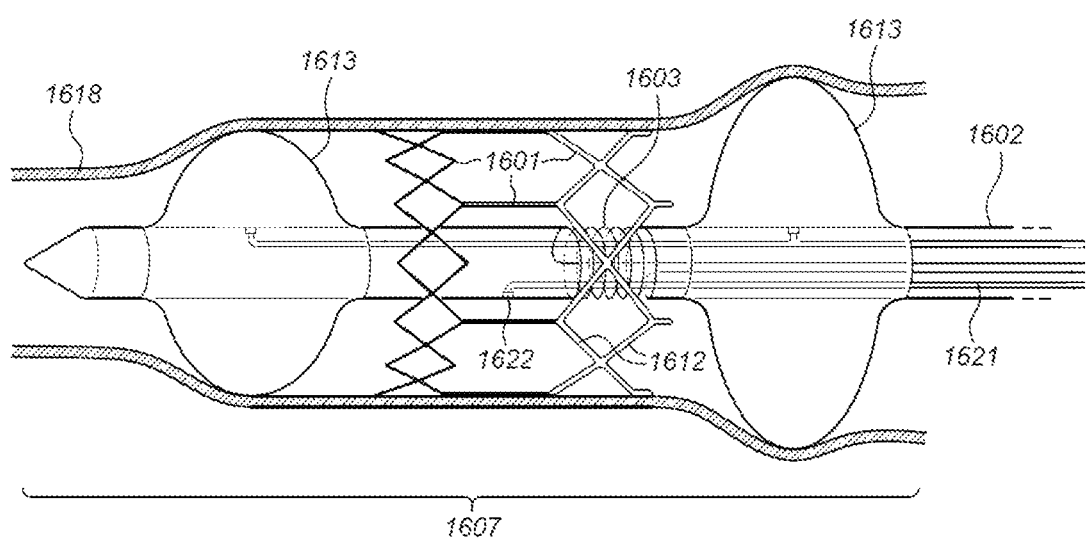
FIG. 16 schematically represents a vessel, an embodiment of an implant device according to the present invention, and an embodiment of the distal end of a catheter shaft according to the present invention.

FIG. 16 schematically represents a vessel 1618, an embodiment of an implant device 1601 according to the present invention, and an embodiment of the distal end 1607 of a catheter shaft 1602 according to the present invention comprising two balloons 1613 with cylindrical symmetry with respect to the longitudinal axis of the catheter and adapted for complete circumferential surface contact with the vessel 1618. The catheter shaft 1602 further comprises an emitter coil 1603 located in between the two balloons 1613. The catheter shaft 1602 further comprises a transfer lumen 1621, which is in communication with the exterior region of the balloons 1613 by means of an opening 1622 in the catheter shaft in between the two balloons. The emitter coil 1603 is positioned near the implant device 1601, preferably surrounded by the implant device 1601. Inflation of the balloons 1613 can align the central axes of the emitter coil and the pick-up coil formed by the circumferential structure coaxially and can stop the fluid flow in the vessel. For certain vessels and/or regions in vessels, the two balloons can have a different shape and or size in order to reach complete circumferential surface contact. Fluid, e.g. blood, in the region spanned by the vessel 1618 and the exterior regions of the two inflated balloons 1613 can be replaced with another harmless fluid by means of the transfer lumen 1621, thereby reducing the chance of clots due to heat from the ablation region 1612.

In an embodiment of the present invention, the implant device comprises a central axis, and the implant device is radially expandable in directions perpendicular to its central axis, and at least one of the balloons is uninflated and designed for support of the unexpanded implant device, and at least one of the balloons designed for support of the implant device is able to withstand pressures sufficient to radially expand the implant device. The catheter may comprise a movable protector sheath around the catheter shaft suitable for protection of the unexpanded implant device supported by an uninflated balloon.

Figure 17:
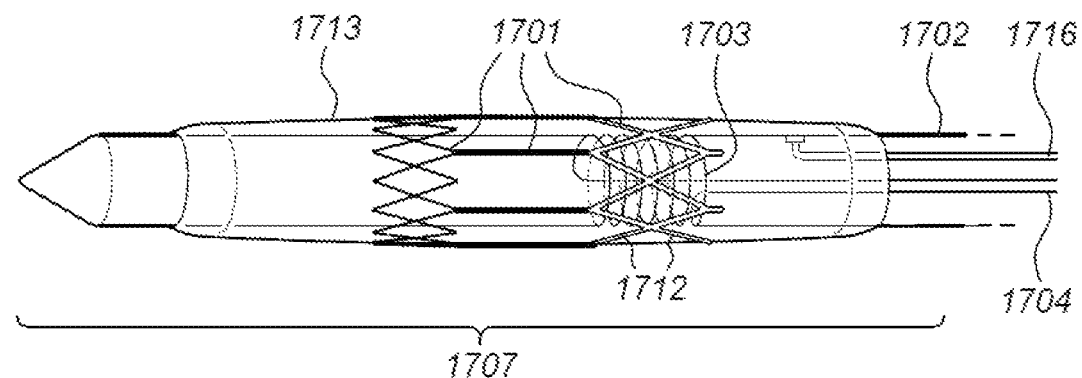
FIGS. 17 and 18 schematically represent the distal end of a catheter shaft according to the present invention.
Figure 18:
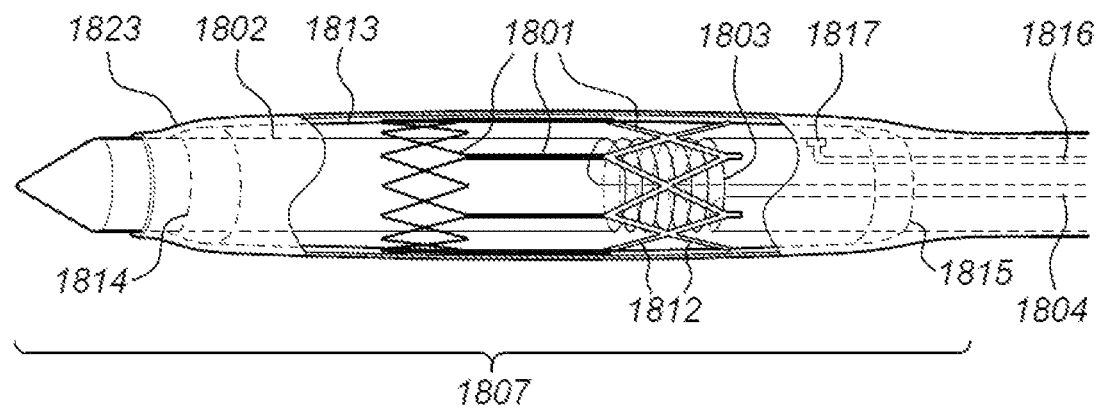

FIGS. 17 and 18 schematically represent the distal end 1707, 1807 of a catheter shaft 1702, 1802 according to the present invention comprising an emitter coil 1703, 1803, electrical wiring 1704, 1804, an uninflated balloon 1713, 1813, an inflation lumen 1716, 1816, a connection 1717, 1817 to bring the inflation lumen 1716, 1816 in communication with the interior of the balloon 1713, 1813, and an unexpanded implant device 1701, 1801 supported by the uninflated balloon 1713, 1813. In FIG. 18, the catheter further comprises a movable protector sheath 1823 around the catheter shaft 1802, uninflated balloon 1813, and implant device 1801.

The implant device of the present invention can also be inserted in the vessel (e.g. the vein), positioned, radially expanded by inflation of a supporting balloon, mounted in the wall of the vessel, and its ablation region 1712, 1812 heated, with a single insertion of a single catheter in the patient's body. The supporting balloon may also be used to thermally insulate the fluid in the vessel, e.g. the blood in the vein, from the ablation region and/or to stop the fluid flow in the vessel.

In an embodiment of the present invention, the implant device comprises a thermoactive coating with an activation temperature above a predefined temperature, preferably above 37° C., more preferably above 40° C., such as 41° C., 42° C., 43° C., 44° C., 45° C., to activate the thermoactive coating simultaneous to and/or after heating of the ablation region.

In an embodiment of the present invention, the implant device comprises substances which are released from the implant device upon or after activation of the thermoactive coating.

In an embodiment of the present invention, the emitter coil and/or pick-up coil comprise a biocompatible metal, preferably nitinol.

EXAMPLE

The example pertains to an embodiment of the present invention for treating cancer or tumors by thermotherapy as illustrated in FIG. 18, in which the distal end 1807 of the catheter shaft 1802 comprises
 a. an emitter coil 1803 comprising a central axis substantially parallel to the longitudinal axis of the catheter and connected to electrical wiring 1804 extending from the distal end 1807 to the proximal end, whereby the electrical wiring 1804 can be connected at or near the proximal end of the catheter shaft to an electric power source,
 b. an uninflated balloon 1813 with two air-tight connections 1814 and 1815 to the catheter shaft 1802, the balloon comprising an anticoagulant coating comprising heparin sulphate,
 c. an inflation lumen 1816 in communication with the interior of the balloon 1813 by means of an opening 1817 in the catheter shaft 1802 and which can be connected at or near the proximal end to a pressurizing means,
 d. an implant device 1801, radially expandable in directions perpendicular to its central axis and supported by the uninflated balloon, whereby the ablation region 1812 of the implant device surrounds the emitter coil 1803, and whereby the implant device comprises a thermoactive coating with an activation temperature preferably above 37° C., more preferably above 40° C., such as 41° C., 42° C., 43° C., 44° C., 45° C.,
 e. a movable protector sheath 1823, covering the catheter shaft 1802, the uninflated balloon 1813, and the unexpanded implant device 1801.

The balloon 1813 and the air-tight connections 1814, 1815 are further adapted
 a. to withstand pressures sufficient to radially expand the implant device 1801,
 b. to yield upon inflation an outermost exterior region of the balloon 1813 with substantial cylindrical symmetry,
 c. for complete circumferential surface contact with a vein,
 d. to withstand heating of the ablation region 1812, and
 e. to thermally insulate the ablation region from blood in the vein.

A guidewire or guiding tip can be used to bring the distal end 1807 of the catheter shaft 1802 in the vein of the patient, whereby the ablation region 1812 of the unexpanded implant device 1801 is positioned at a location where the vein leads to a tumor or in close vicinity of the tumor. The movable protector sheath 1823 ensures that during insertion of the catheter in the patient's body, the implant device 1801 cannot come into contact with any veins. Once the catheter is positioned as desired, the movable protector sheath 1823 is retracted in the direction of the proximal end of the catheter shaft, thereby exposing the uninflated balloon 1813 and unexpanded implant device 1801. The interior of the balloon 1813 is in communication with the inflation lumen 1816 by means of an opening 1817 in the catheter shaft 1802. With a pressurizing means connected to the proximal end of the inflation lumen 1816, the balloon 1813 can be inflated, thereby radially expanding the implant device 1801 as well.

As illustrated in FIG. 13, inflation of the balloon 1313
 a. mounts the implant device 1301 in the vein 1318,
 b. stops blood flow in the vein 1318,
 c. thermally insulates blood in the vein 1318 from the ablation region 1312 of the implant device 1301,
 d. ensures substantial parallel alignment of the central axes of the emitter coil 1303 and the pick-up coil of the implant device 1301,
 e. even ensures near perfect coaxial alignment of the central axes of the emitter coil 1303 and the pick-up coil 1319 of the implant device 1301,
 f. positions the emitter coil 1303 inside the ablation region 1312 of the implant device 1301.

The chance of blood clot formation in the vein 1318 is limited due to the anticoagulant coating of the balloon 1313 comprising heparin sulphate. The emitter coil 1303 can be connected to the electric power source by means of electrical wiring 1304 extending from the distal end to the proximal end of the catheter shaft 1302. With an alternating current of the electric power source, the emitter coil 1303 emits a time-varying magnetic field, which is optimally coupled to the pick-up coil of the implant device 1301 due to the absence of body tissue in between the emitter and pick-up coils and due to the near perfect coaxial alignment of the central axes of the emitter and pick-up coils. The time-varying magnetic field induces a current in the pick-up coil, which is converted in the ablation region 1312 into heat by Joule heating. As blood cannot reach the ablation region 1312 due to the inflated balloon 1313, the heat cannot be drained by natural or forced convection. In order to limit the chance of blood clot formation even more, the balloon 1313 can be a perfusion balloon, or the catheter can comprise a perfusion lumen. When the ablation region reaches a sufficiently high temperature, the thermoactive coating of the implant device is released, to produce a lesion of limited necrosis and/or neurotoxicity during the ablation.

A prior introduction of bioprobes coupling to the tumor cells, can further lead to specific heating of the tumor cells.

In the above embodiments, references are made to uses of the present invention whereby the implant device can implanted in a blood vessel, e.g. a vein or artery, for subsequent treatment. However, it should be clear that the present system also has its applications for other types of vessels, e.g. urinary tracts, lymphatic vessels, etc.

The invention claimed is:

1. A system for treating cancer or tumors by thermotherapy, comprising:
 an expandable implant device, an excitation catheter and an electric power source, wherein the implant device is configured for circumferentially subtending a vessel upon expansion of the implant device in said vessel, the implant device comprising a set of cross-connected conductors forming a circumferential structure with openings in between the conductors, said openings having a minimal opening distance of at least 2 mm with the implant device in an expanded configuration, wherein the excitation catheter comprises a longitudinal shaft with a distal end, a proximal end, and a longitudinal body in between, wherein the catheter comprises a longitudinal axis along the longitudinal shaft, and wherein the catheter further comprises an emitter coil at or near the distal end, and wherein the longitudinal body of the catheter further comprises a wiring lumen comprising electrical wiring extending from the distal end to the proximal end, and wherein the electrical wiring is connected at or near the distal end with the emitter coil, and wherein the electric power source is configured to be connected to the wiring via the proximal end of the catheter shaft for generation of a time-varying magnetic field with the emitter coil; a set of bioprobes, each bioprobe comprising a magnetic susceptor and at least one ligand; and wherein the implant device comprises cavities at an outer surface of the implant device, said cavities being provided with the set of bioprobes, said cavities being closed off with a thermodegradable cover, in a manner that the bioprobes are released from the cavities upon heating of the implant device.

2. The system according to claim 1, wherein at least one bioprobe of the set of bioprobes comprises a ligand which targets mitochondria.

3. The system according to claim 1, wherein at least one bioprobe comprises a magnetic energy susceptive particle.

4. The system according to claim 1, wherein the magnetic susceptor of the bioprobes comprises iron oxide, iron-cobalt (FeCo) and/or glass (SiO2).

5. The system according to claim 1, wherein the ligand of at least one bioprobe is an antibody.

6. The system according to claim 1, wherein the ligand is selected from the list of polyclonal antibodies, monoclonal antibodies, chimeric antibodies, humanized antibodies, human antibodies, recombinant antibodies, bispecific antibodies, antibody fragments, scFVs 480, Fabs 472, dsFVs 474, recombinant single chain antibody fragments, and peptides.

7. The system according to claim 1, wherein the ligand is selected to target a disease marker, said marker selected from the list of cell surface markers, members of the MUC-type mucin family, an epithelial growth factor (EGFR) receptor, a carcinoembryonic antigen (CEA), a human carcinoma antigen, a vascular endothelial growth factor (VEGF) antigen, family antigen, a T/Tn antigen, a hormone receptor, growth factor receptors, a cluster designation/differentiation (CD) antigen, a proliferation marker, an adhesion molecule, a proteinase involved in degradation of extracellular matrix, a malignant transformation related factor, DF3, 4F2, MGFM antigens, breast tumor antigen CA 15-3, calponin, cathepsin, CD 31 antigen, proliferating cell nuclear antigen 10 (PC 10), pS2, a type of anti-idiotypic mAB, a type of ganglioside mimic, a type of a cellular adhesion molecule, a type of cancer antigen (CA), a type of a matrix metalloproteinase, a type of glycoprotein antigen, a type of melanoma associated antigen (MAA), a proteolytic enzyme, a calmodulin, a member of tumor necrosis factor (TNF) receptor family, a type of angiogenesis marker, a melanoma antigen recognized by T cells (MART) antigen, a member of melanoma antigen encoding gene (MAGE) family, a prostate membrane specific antigen (PMSA), a small cell lung carcinoma antigen (SCLCA), a tumor suppressor gene antigen, a cell cycle regulator antigen, an oncogene antigen, an oncogene receptor antigen, and an apoptosis-related factor.

8. The system according to claim 1, wherein the catheter shaft comprises a guiding tip and/or a guiding lumen for sliding the catheter over a guidewire.

9. The system according to claim 1, wherein the implant device comprises a radially expandable heating region and a radially expandable ring of open diamond-shaped elements which are connected to the heating region by struts.

10. The system according to claim 1, wherein the implant device comprises bioresorbable material.

11. The system according to claim 1, wherein the emitter coil comprises a flux-enhancing material.

12. A method for treating a tumor or cancerous cells in a patient by thermotherapy, comprising the steps of:
    implanting an expandable implant device in a vessel with the implant device configured to circumferentially subtend the vessel upon expansion of the implant device in said vessel, the implant device comprising a set of cross-connected conductors forming a circumferential structure with openings in between the conductors, said openings having a minimal opening distance of at least 2 mm with the implant device in an expanded configuration, wherein the vessel and the implant position of the implant device in the vessel is pre-selected on the basis of distance to the tumor or cancerous cells and/or on the basis of nutrient supply flow to the tumor or cancerous cells;
    wherein the implant device comprises cavities at an outer surface of the implant device, the cavities being provided with one or more bioprobes and being closed off with a thermodegradable cover, wherein each bioprobe comprises a magnetic susceptor and at least one ligand;
    inserting an excitation catheter in the patient, wherein the excitation catheter comprises a longitudinal shaft with a distal end, a proximal end, and a longitudinal body in between, wherein the catheter comprises a longitudinal axis along the longitudinal shaft, and wherein the catheter further comprises an emitter coil at or near the distal end, and wherein the longitudinal body of the catheter further comprises a wiring lumen comprising electrical wiring extending from the distal end to the proximal end, and wherein the electrical wiring is connected at or near the distal end with the emitter coil,
    positioning the emitter coil of the catheter within the expanded implant device, and
    energizing the emitter coil to emit an alternating magnetic field, generating a current flow in the conductors of the implant device, heating the implant device with generated energy and re-radiating an alternating magnetic field to surrounding tissue;
    wherein the one or more bioprobes are released from the cavities and heated upon heating of the implant device by the generated energy.

* * * * *